(12) United States Patent
Stein

(10) Patent No.: US 12,082,944 B2
(45) Date of Patent: Sep. 10, 2024

(54) SYSTEM AND METHOD FOR MONITORING NERVE ACTIVITY WITHIN A TRACHEA OF A PATIENT

(71) Applicant: Stryker Corporation, Kalamazoo, MI (US)

(72) Inventor: Richard Evan Stein, Flower Mound, TX (US)

(73) Assignee: Stryker Corporation, Kalamazoo, MI (US)

(*) Notice: Subject to any disclaimer, the term of this patent is extended or adjusted under 35 U.S.C. 154(b) by 693 days.

(21) Appl. No.: 17/286,223

(22) PCT Filed: Oct. 31, 2019

(86) PCT No.: PCT/US2019/059063
§ 371 (c)(1),
(2) Date: Apr. 16, 2021

(87) PCT Pub. No.: WO2020/092708
PCT Pub. Date: May 7, 2020

(65) Prior Publication Data
US 2021/0338164 A1    Nov. 4, 2021

Related U.S. Application Data

(60) Provisional application No. 62/753,367, filed on Oct. 31, 2018.

(51) Int. Cl.
| | | |
|---|---|---|
| *A61M 16/04* | (2006.01) | |
| *A61B 5/00* | (2006.01) | |
| *A61B 5/294* | (2021.01) | |
| *A61B 5/296* | (2021.01) | |
| *A61B 5/388* | (2021.01) | |
| *A61B 5/389* | (2021.01) | |

(52) U.S. Cl.
CPC ............ *A61B 5/6852* (2013.01); *A61B 5/294* (2021.01); *A61B 5/296* (2021.01); *A61B 5/388* (2021.01);
(Continued)

(58) Field of Classification Search
CPC .......................... A61B 5/6852; A61M 16/0402
(Continued)

(56) References Cited

U.S. PATENT DOCUMENTS

| | | |
|---|---|---|
| 5,070,859 A | 12/1991 | Waldvogel |
| 6,272,936 B1 | 8/2001 | Oreper et al. |

(Continued)

FOREIGN PATENT DOCUMENTS

| | | |
|---|---|---|
| KR | 20180042766 A | 4/2018 |
| WO | 2004073518 A1 | 9/2004 |

OTHER PUBLICATIONS

Chiang, Feng-Yu et al., "Comparison of EMG Signals Recorded By Surface Electrodes on Endotracheal Tube and Thyroid Cartilage During Monitored Thyroidectomy", The Kaohsiuunh Journal of Medical Sciences, vol. 33, Issue 10, pp. 503-509.
(Continued)

*Primary Examiner* — Nadia A Mahmood
(74) *Attorney, Agent, or Firm* — Howard & Howard Attorneys PLLC

(57) ABSTRACT

An intraoperative nerve monitoring system for monitoring nerve activity within a trachea of a patient. The intraoperative nerve monitoring system includes an endotracheal (ET) tube assembly, which includes an ET tube partially inserted within a trachea and a surface electrode wrapped about the ET tube. The ET tube is configured to monitor nerve activity when the ET tube is partially inserted within the trachea and is contacting a target tissue and to output a nerve signal. The intraoperative nerve monitoring system also includes a pressure sensor assembly configured to sense an amount of pressure between the surface electrode and the target tissue and a console including an output device configured to output indicators based on the monitored nerve activity and the sensed amount of pressure to facilitate proper placement of the ET tube in the trachea and to indicate nerve activity.

20 Claims, 23 Drawing Sheets

(52) U.S. Cl.
CPC ............ *A61B 5/389* (2021.01); *A61B 5/6885* (2013.01); *A61M 16/0402* (2014.02); *A61B 2505/05* (2013.01); *A61B 2562/0209* (2013.01)

(58) Field of Classification Search
USPC ........................................................ 600/301
See application file for complete search history.

(56) References Cited

U.S. PATENT DOCUMENTS

| | | |
|---|---|---|
| 8,740,783 B2 | 6/2014 | Gharib et al. |
| 2011/0190596 A1* | 8/2011 | Hacker ............. A61M 16/0434 600/301 |

OTHER PUBLICATIONS

English language abstract and machine-assisted English translation for KR 20180042766 A extracted from espacenet.com database on Apr. 28, 2021, 6 pages.

International Search Report for Application No. PCT/US2019/059063 dated Nov. 3, 2020, 4 pages.

Julien, N. et al., "Vagal and Recurrent Laryngeal Nerves Neuromonitoring During Throidectomy and Parathyroidectomy: A Prospective Study", European Annals of Otorhinolaryngology, Head and Neck Diseases, Elsevier, Amsterdam, NL, vol. 134, No. 2, Dec. 27, 2016, pp. 77-82.

Tsai, Cheng-Jing et al., Electromyographic Endotracheal Tube Placement During Thyroid Surgery in Neuromonitoring of Recurrent Laryngeal Nerve:, The Kaohsiuunh Journal of Medical Sciences, vol. 27, Issue 3, pp. 96-101.

* cited by examiner

SYSTEM AND METHOD FOR MONITORING NERVE ACTIVITY WITHIN A TRACHEA OF A PATIENT

PRIORITY

This application is a National Stage of International Patent Application No. PCT/US2019/059063, filed on Oct. 31, 2019, which claims priority to and all advantages of U.S. Provisional Application No. 62/753,367, which was filed on Oct. 31, 2018, the disclosures of which are specifically incorporated by reference.

BACKGROUND

Endotracheal (ET) tubes are typically used to ensure that a patient maintains an open airway during a medical procedure. There remains a need in the art for an interoperative nerve monitoring system that allows for accurate monitoring of nerve activity during medical procedures requiring the use of ET tubes.

SUMMARY OF THE DISCLOSURE

A method of operating an intraoperative nerve monitoring system for monitoring nerve activity within a trachea of a patient is provided. The intraoperative nerve monitoring system includes a console having a controller and an output device and an endotracheal (ET) tube assembly. The ET tube assembly includes an ET tube having an outer circumferential surface, a surface electrode wrapped about a portion of the outer circumferential surface of the ET tube, and a pressure sensor assembly coupled to the outer circumferential surface of the ET tube. The method of operating the intraoperative nerve monitoring system includes steps of inserting the ET tube within the trachea of the patient; sensing, with the pressure sensor assembly, an amount of pressure between the surface electrode and a target tissue; determining, with the controller, whether the amount of pressure exceeds a pressure threshold; outputting, with the output device, a first indicator based on whether the amount of pressure exceeds the pressure threshold to facilitate proper placement of the ET tube in the trachea; monitoring, with the surface electrode, nerve activity within the trachea while the ET tube is inserted within the trachea; and outputting, with the output device, a second indicator based on the nerve activity.

An intraoperative nerve monitoring system for monitoring nerve activity within a trachea of a patient is provided. The intraoperative nerve monitoring system includes an endotracheal (ET) tube assembly, which includes an ET tube comprising an outer circumferential surface and a length sufficient for insertion within a trachea of a patient, the ET tube being configured to be at least partially inserted within the trachea. The ET tube assembly also includes a surface electrode and a pressure sensor assembly. The surface electrode is wrapped about a portion of the outer circumferential surface of the ET tube and is configured to monitor nerve activity when the ET tube is at least partially inserted within the trachea and contacting the target tissue and to output a nerve signal that corresponds to the nerve activity. The pressure sensor assembly is coupled to the outer circumferential surface of the ET tube and is configured to sense an amount of pressure between the surface electrode and the target tissue and output a pressure signal based on the amount of pressure. The intraoperative nerve monitoring system also includes a console, which includes a controller and an output device. The controller is configured to receive the pressure signal and the nerve signal and output an output signal based on the pressure signal and the nerve signal. The output device is configured to receive the output signal and output a first indicator and a second indicator based on the output signal, the first indicator being configured to facilitate proper placement of the ET tube in the trachea and the second indicator being indicative of the nerve activity.

An endotracheal (ET) tube assembly configured for nerve monitoring and pressure sensing is provided. The ET tube assembly includes an ET tube comprising an outer circumferential surface and a length sufficient for insertion within a trachea of a patient, the ET tube being configured to be at least partially inserted within the trachea. The ET tube assembly also includes a surface electrode and a pressure sensor assembly. The surface electrode is wrapped about a portion of the outer circumferential surface of the ET tube and is configured to contact a target tissue and monitor nerve activity when the ET tube is at least partially inserted within the trachea. The pressure sensor assembly coupled to the outer circumferential surface of the ET tube, the pressure sensor assembly being configured to sense an amount of pressure between the surface electrode and the target tissue.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination with one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows.

DETAILED DESCRIPTION

Figure 1A:
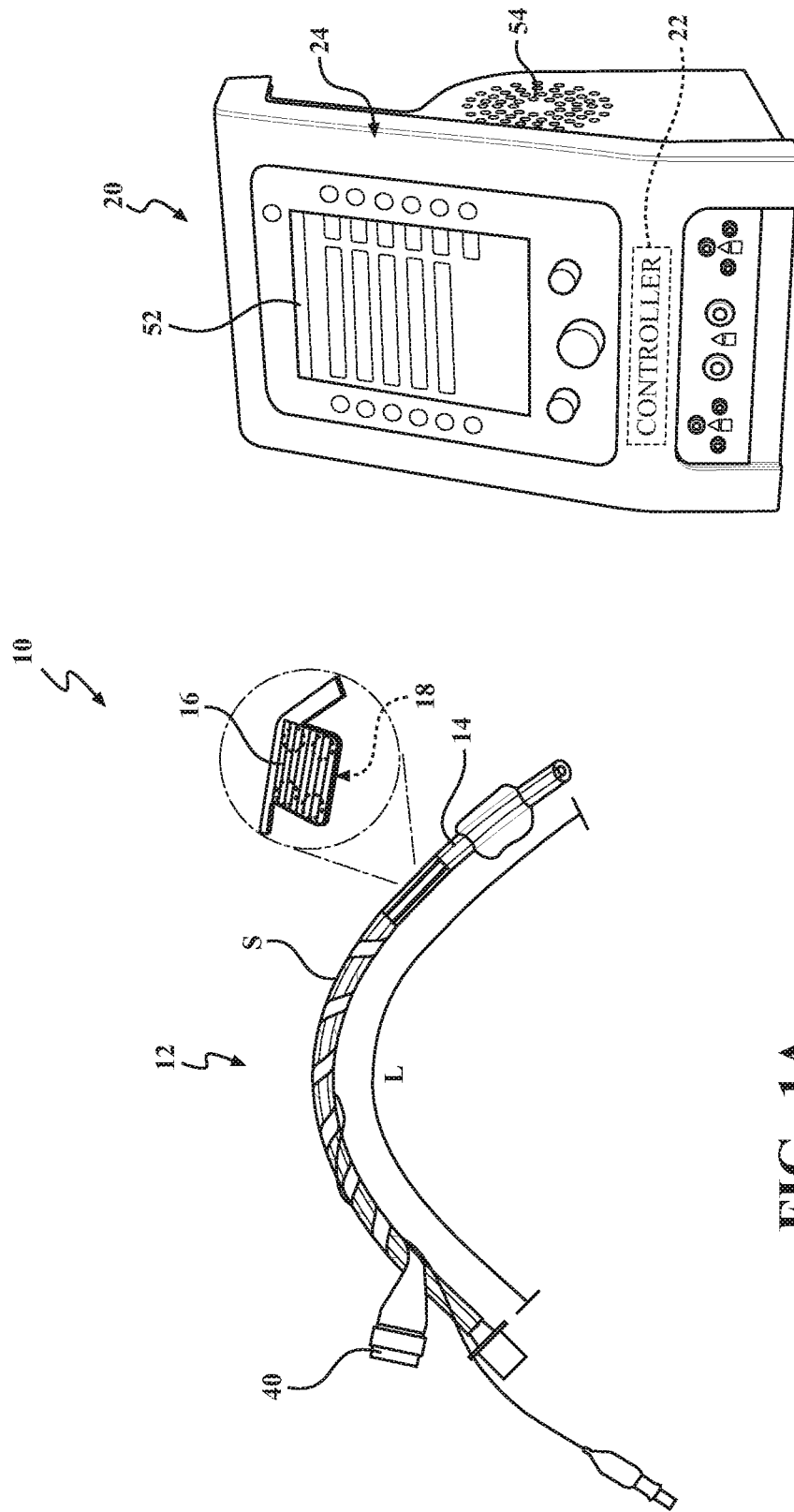
FIG. 1A is a perspective view of an endotracheal (ET) tube assembly and a console of an intraoperative nerve monitoring system.
Figure 2:
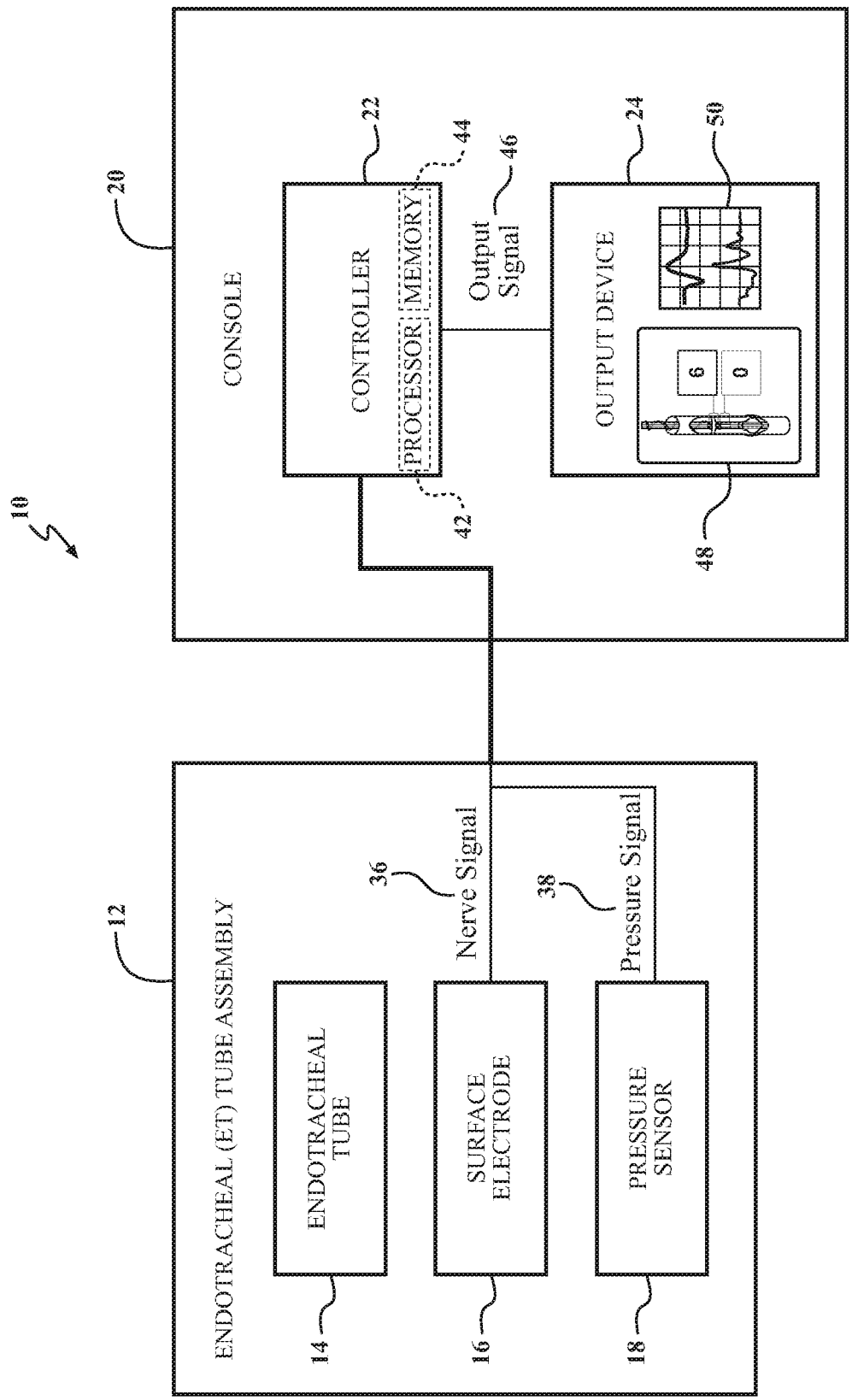
FIG. 2 is a schematic view of the intraoperative nerve monitoring system.

Referring to FIGS. 1A and 2, an intraoperative nerve monitoring system 10 for monitoring nerve activity within a trachea 26 of a patient is shown. Referring to FIG. 2, the intraoperative nerve monitoring system 10 includes an endotracheal (ET) tube assembly 12, which includes an endotracheal (ET) tube 14, a surface electrode 16, and a pressure sensor assembly 18. Additionally, the intraoperative nerve monitoring system 10 includes a console 20, which includes a controller 22 and an output device 24.

Figure 4A:
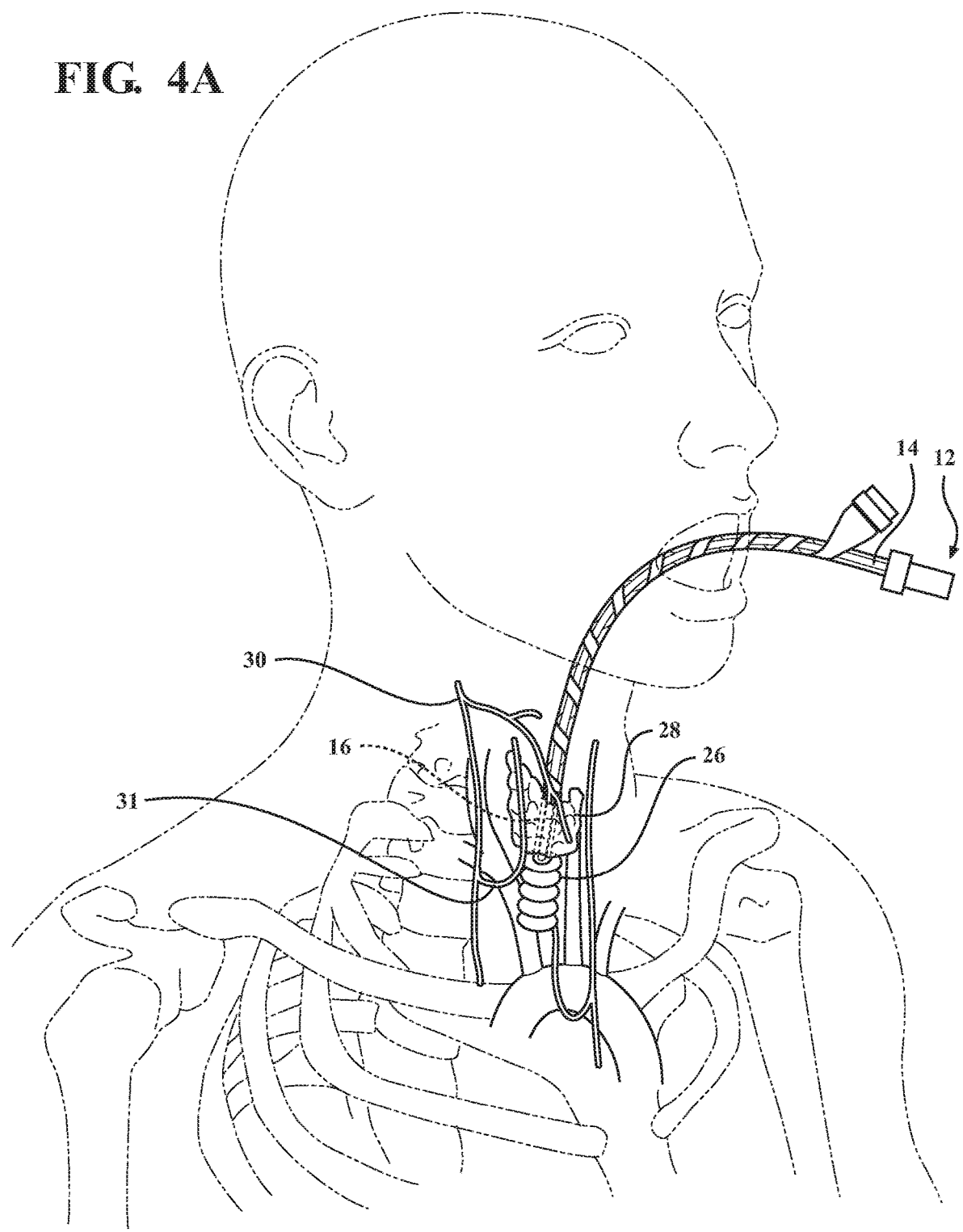
FIG. 4A is a perspective view of the ET tube assembly being inserted within a trachea of a patient.

As shown in FIG. 1A, the ET tube 14 of the ET tube assembly 12 includes a length L. Referring to FIG. 4A, the ET tube 14 is configured to be at least partially inserted within a trachea 26 of a patient. As such, the length L is sufficient for insertion within the trachea 26 of the patient. Additionally, referring to FIG. 4B, the ET tube 14 may be inserted within the trachea 26 such that the ET tube 14 is rotatable clockwise and counterclockwise and slidable proximally and distally within the trachea 26, as illustrated by the directional arrows A1, A2, A3, and A4, respectively.

Furthermore, the ET tube 14 may comprise, consist essentially of, or consist of, a compliant material, such as a polymer. As such, the ET tube 14 may comply with a shape of the trachea, allowing the ET tube 14 to be at least partially inserted within the trachea 26. The compliant material may comprise one or more polymers. For example, in some instances, the compliant material is selected from elastomers, thermoplastics, thermoplastic elastomers, and combinations thereof.

Also shown in FIG. 1A, the ET tube 14 of the ET tube assembly 12 includes an outer circumferential surface S. In FIG. 1A, the surface electrode 16 is wrapped about a portion of the outer circumferential surface S of the ET tube 14 and the pressure sensor assembly 18 is coupled to the outer circumferential surface S. While the surface electrode 16 is shown as being wrapped helically to the ET tube 14, the surface electrode 16 may alternatively be wrapped in other manners. Alternately, the surface electrode 16 and the pressure sensor assembly 18 may be coupled to the outer circumferential surface S without any specific wrapping arrangement.

The surface electrode 16 is configured to monitor nerve activity when the ET tube 14 is at least partially inserted within the trachea 26. The surface electrode 16 is also configured to output a nerve signal 36 corresponding to the monitored nerve activity, as shown in FIG. 2. In some instances, the nerve signal 36 may be a voltage signal, wherein the voltage of the nerve signal 36 corresponds to the nerve activity.

Figure 4B:
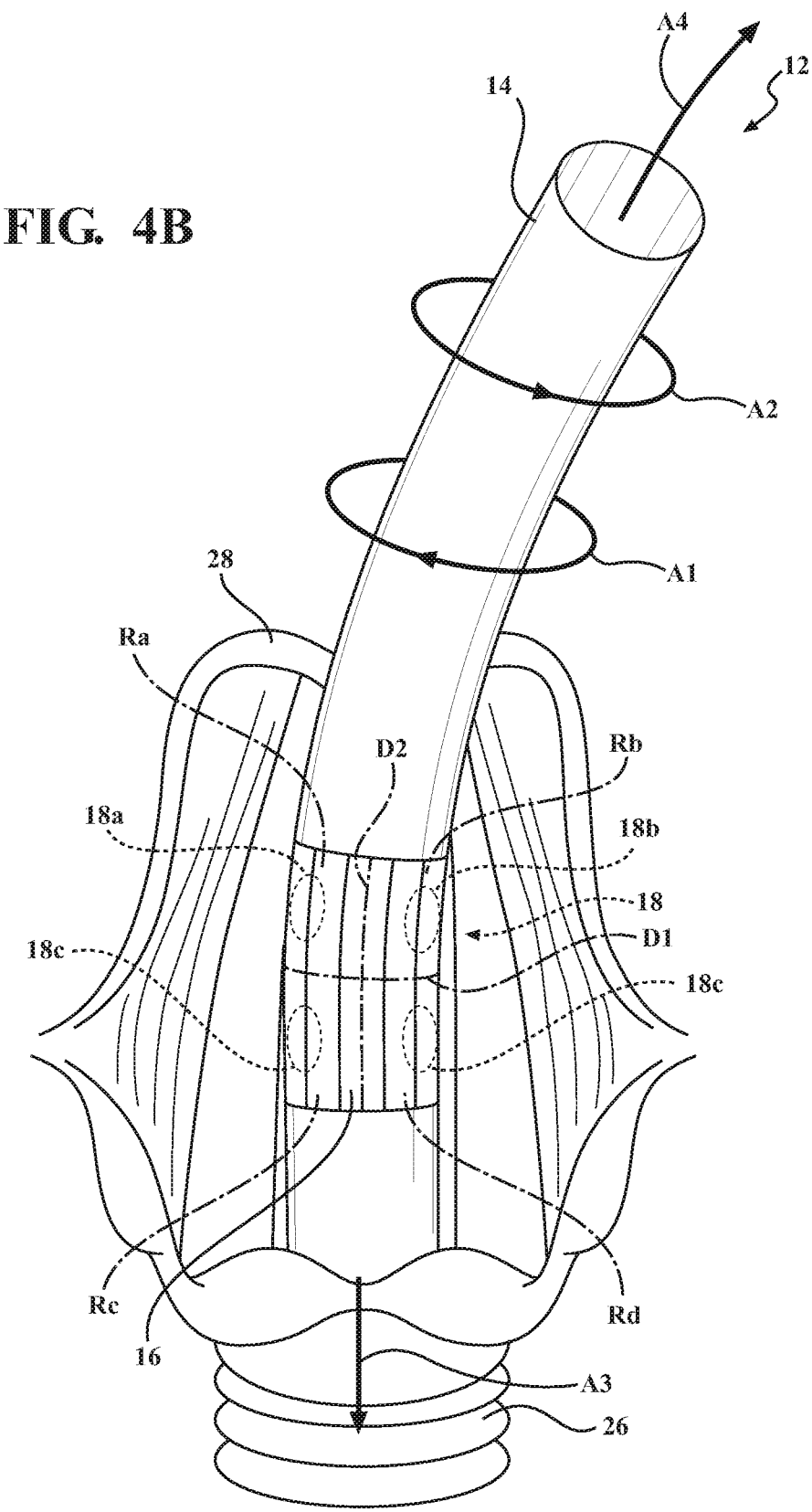
FIG. 4B is a perspective view of the ET tube assembly contacting a target tissue of a patient.

Referring to FIGS. 4A and 4B, the ET tube 14 may be inserted within the trachea 26 such that the surface electrode 16 contacts a target tissue 28. In FIGS. 4A and 4B, the target tissue 28 is a laryngeal muscle (and may be referred to herein as laryngeal muscle 28) and the surface electrode 16 is configured to monitor the nerve activity of the vagus nerve 30 and/or the laryngeal nerve 31. However, in other instances, the target tissue 28 may be a tissue other than the laryngeal muscle 28 and the surface electrode 16 may be configured to monitor the nerve activity of a nerve other than the vagus nerve 30 and/or the laryngeal nerve 31. Furthermore, the surface electrode 16 may be configured to monitor the nerve activity of any number of nerves.

The surface electrode 16 may be any suitable device for monitoring the nerve activity. For example, the surface electrode 16 may include a plurality of electrode contacts configured to sense electromyography (EMG) signals to monitor the nerve activity.

The surface electrode 16 may be coupled to the outer circumferential surface S using any suitable means. For example, in FIG. 1A, the surface electrode 16 is wrapped about a portion of the outer circumferential surface S of the ET tube 14. In another instance, the surface electrode 16 may be affixed to the ET tube 14 using an adhesive. In yet another instance, the surface electrode 16 may be integral to the outer circumferential surface S of the ET tube 14.

The pressure sensor assembly 18 is configured to sense an amount of pressure between the surface electrode 16 and the target tissue 28. As shown in FIG. 2, the pressure sensor assembly 18 is also configured to output a pressure signal 38 corresponding to the sensed amount of pressure. In some instances, the pressure signal 38 may be a voltage signal, wherein the voltage of the pressure signal 38 corresponds to the sensed amount of pressure.

Figure 1B:
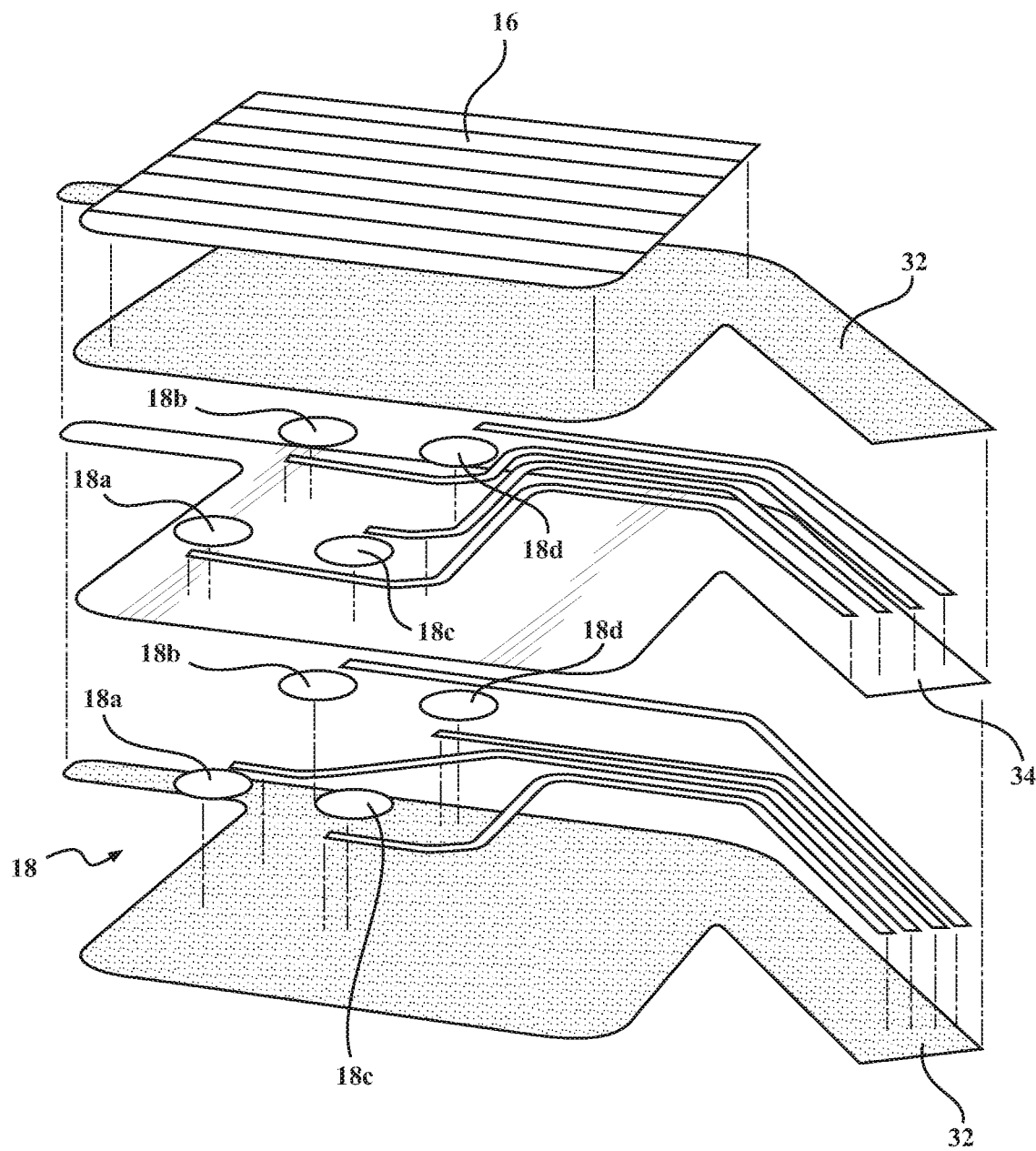
FIG. 1B is an exploded view of a surface electrode and a pressure sensor assembly of the ET tube assembly.

The pressure sensor assembly 18 may be coupled to the outer circumferential surface S of the ET tube 14 using any suitable means. For example, in FIG. 1A, the pressure sensor assembly 18 is coupled to surface electrode 16, which is wrapped about a portion of the outer circumferential surface S. An example coupling of the pressure sensor assembly 18 to the surface electrode 16 is illustrated in FIG. 1B. As shown, the ET tube assembly 12 includes two substrate layers 32 and an adhesive layer 34, which are configured to couple the pressure sensor assembly 18 to the surface electrode 16. In various instances, the pressure sensor assembly 18 may be coupled to the surface electrode 16 using any suitable means. For example, in some instances, the ET tube assembly 12 may include a greater or lesser number of substrate layers 32 and adhesive layers 34 for coupling the pressure sensor assembly 18 to the surface electrode 16. In still other instances, the ET tube assembly 12 may omit the substrate layers 32 and/or the adhesive layers 34. Furthermore, in some instances, the pressure sensor assembly 18 may be directly coupled to the outer portion of the outer circumferential surface S without being coupled to the surface electrode 16. For example, the pressure sensor assembly 18 may be directly affixed to the outer circumferential surface S using an adhesive. In certain instances, the pressure sensor assembly 18 may be positioned such that the pressure sensor assembly 18 is closer to the lumen of the ET tube 14 than to the surface electrode 16.

The pressure sensor assembly 18 may include a plurality of pressure sensors, such as two or more pressure sensors. For example, in FIG. 1B, the pressure sensor assembly 18 includes four pressure sensors 18a, 18b, 18c, 18d. The pressure sensor assembly 18 may be configured to sense the amount of pressure between the surface electrode 16 and the target tissue 28 by sensing an amount of pressure with each of the four pressure sensors 18a, 18b, 18c, 18d. For instance, each pressure sensor 18a, 18b, 18c, 18d may be configured to sense an amount of pressure between the surface electrode 16 and the target tissue 28 at a region on the outer circumferential surface S. For example, referring to FIG. 4B, the pressure sensors 18a, 18b, 18c, and 18d are configured to sense the amount of pressure between the surface electrode 16 and the target tissue 28 at regions Ra, Rb, Rc, Rd, respectively. As such, the pressure sensor assembly 18 is able to sense the amount of pressure between the surface electrode 16 and the target tissue 28 by sensing the amount of pressure at the regions Ra, Rb, Rc, Rd.

As shown in FIG. 4B, the regions Ra, Rb, Rc, and Rd are divided by dividers D1 and D2 such that regions Ra and Rb are generally above the regions Rc and Rd. Furthermore, the regions Ra and Rc are angularly offset from the regions Rb and Rd. In other instances, the regions Ra, Rb, Rc, and Rd may be arranged using alternative means. For example, in some instances, the regions Ra and Rc may be vertically offset from the regions Rb and Rd. Similarly, the regions Ra and Rb may be horizontally offset from the regions Rc and Rd. In other instances, the regions Ra, Rb, Rc, and Rd may be arranged vertically along the outer circumferential surface S such that the region Ra is generally above the region Rb, which is generally above the region Rc, which is generally above the region Rd. Similarly, the regions Ra, Rb, Rc, and Rd may be arranged horizontally along the outer circumferential surface S. In still other instances, the regions Ra, Rb, Rc, and Rd may be arranged such that a different number of regions are generally above or angularly offset from one another. For instance, region Ra may be generally above the regions Rb, Rc, and Rd, which may be arranged horizontally. Similarly, region Ra may be angularly offset from regions Rb, Rc, and Rd, which may be arranged vertically. Additionally, in some instances, such as the instance of FIG. 4B, the regions may be separate, distinct regions on the outer circumferential surface S. However, in other instances, the regions on the outer circumferential surface S may overlap. Furthermore, the regions may be of any suitable size and the sizes of each region may be independent from one another.

Additionally, while the regions are described herein as regions on the outer circumferential surface S, the regions may be arranged such that the regions correspond to and/or include regions of the surface electrode 16. For example, the regions Ra, Rb, Rc, and Rd are regions on the outer circumferential surface S, but may also be described herein as a top-left, a top-right, a bottom-left, and a bottom-right region of the surface electrode 16. As such, while the pressure sensor assembly 18 is described as being configured to determine the amount of pressure between the surface electrode 16 and the target tissue 28 at a plurality of regions on the outer circumferential surface S, the pressure sensor assembly 18 may also be described as being configured to determine the amount of pressure between a plurality of regions of the surface electrode 16 and the target tissue 28.

The number of pressure sensors included by the pressure sensor assembly 18 and the number of regions may vary. For example, the number of pressure sensors and the number of regions may not be equivalent to four. Furthermore, the number of pressure sensors and the number of regions may not be equivalent to one another. For example, referring to FIG. 4B, the pressure sensor assembly 18 need not have four distinct pressure sensors 18a, 18b, 18c, 18d, so long as the pressure sensor assembly 18 is able to distinguish between the amounts of pressure in the four regions Ra, Rb, Rc, and Rd. In such an instance, the pressure sensor assembly 18 may include three distinct pressure sensors for sensing the amounts of pressure in the regions Ra, Rb, Rc, and Rd. Similarly, the pressure sensor assembly 18 may include a number of distinct pressure sensors greater than the number of regions. For instance, the pressure sensor assembly may include eight distinct pressure sensors such that the amount of pressure in each of the four regions Ra, Rb, Rc, and Rd is sensed by two of the pressure sensors for added resolution.

As such, the number of regions and/or pressure sensors is not particularly limited. In addition, the positioning of the sensors relative to the regions and the arrangement of the sensors generally is not limited.

The pressure sensor assembly 18 may include any suitable sensor for sensing the amount of pressure. For example, in FIG. 1B, the pressure sensors 18a, 18b, 18c, 18d are illustrated as resistive pressure sensors that include two sections separated by the adhesive layer 34. In some instances, the pressure sensors 18a, 18b, 18c, 18d may be like the pressure sensors shown in U.S. Pat. No. 6,272,936 B1, filed on Feb. 20, 1998, entitled, "Pressure Sensor", the disclosure of which is hereby incorporated by reference in its entirety. In other instances, the pressure sensor assembly 18 may include a strain gauge, a capacitive sensor, or any other sensor suitable for sensing the amount of pressure. For example, the pressure sensor assembly 18 may include one or more layers of pressure sensitive ink embedded between flexible substrate layers, such as the substrate layers 32.

Referring to FIGS. 1A and 2, the intraoperative nerve monitoring system 10 also includes a console 20. Also shown, the console 20 may include a controller 22, which is configured to receive the nerve signal 36 and the pressure signal 38 and output an output signal 46 based on the nerve signal 36 and the pressure signal 38.

As shown in FIG. 2, the controller 22 may include a processor 42 and a memory 44. The processor 42 may be any processor suitable for processing data. For example, the processor 42 may be a processor typically found in a desktop computer. Similarly, the memory 44 may be any memory suitable for storage of data and computer-readable instructions. For example, the memory 44 may be a local memory, an external memory, or a cloud-based memory. The memory 44 may also be a random access memory (RAM), non-volatile RAM (NVRAM), flash memory, or any other suitable form of memory. In some instances, the processor 42 and the memory 44 may be configured to process the nerve signal 36 and the pressure signal 38 and output a corresponding output signal 46.

As previously stated, the controller 22 is configured to receive the nerve signal 36 and the pressure signal 38 from the surface electrode 16 and the pressure sensor assembly 18, respectively. In FIG. 1A, the console 20 may be coupled to the ET tube assembly 12 via the connector 40 such that the controller 22 may receive the nerve signal 36 and the pressure signal 38 from the surface electrode 16 and the pressure sensor assembly 18, respectively, via the connector 40. However, it should be noted that the console 20 may be coupled to the ET tube assembly 12 using wireless transceivers.

Also shown in FIGS. 1A and 2, the console 20 may also include an output device 24. The output device 24 is configured to receive the output signal 46 from the controller 22 and output a first indicator 48 and a second indicator 50 based on the output signal 46. The first indicator 48 is configured to facilitate proper placement of the ET tube 14 in the trachea 26 based on the amount of pressure between the surface electrode 16 and the target tissue 28, and the second indicator 50 is indicative of the nerve activity monitored by the surface electrode 16. The first indicator 48 and the second indicator 50 may include a visual indicator and/or an audible indicator. As such, the output device 24 may include a screen 52 for displaying a visual indicator and a speaker 54 for outputting an audible indicator, as shown in FIG. 1A.

In FIGS. 6A-6E, five examples of the first indicator 48 are shown. In each example, the first indicator 48 includes a numerical indicator 51, which includes at least one number corresponding to the amount of pressure between the surface electrode 16 and the target tissue 28. As previously discussed, this amount of pressure is sensed by the pressure sensor assembly 18. As will be described herein, the numerical indicator 51 facilitates proper placement of the ET tube 14 in the trachea 26 by outputting the at least one number.

The at least one number output by the numerical indicator 51 corresponds to the amount of pressure between the surface electrode 16 and the target tissue 28. In some instances, the at least one number may output the amount of pressure sensed by the pressure sensor assembly 18 using any suitable unit. For instance, the numerical indicator 51 may output the at least one number corresponding to the amount of pressure sensed by the pressure sensor assembly 18 in pascals, volts, pounds per square inch, bars, etc. The at least one number may also be a scaled factor of the amount of pressure sensed by the pressure sensor assembly 18 and may be unit-less. For example, in FIGS. 6A-6E, the numbers 51a, 51b are unit-less and may be any whole number between "0" and "6", inclusive. However, in other instances, the at least one number may be any rational number between any suitable range. Furthermore, each of the numbers 51a, 51b in FIGS. 6A-6E are scaled representations of a range of pressures. For example, each of the numbers from "0" to "6" corresponds to an increasing range of pressures. However, in other instances, the at least one number may correspond to a decreasing range of pressures.

Additionally, as shown in FIGS. 6A-6E, the first indicator 48 may include a diagram 49 of the ET tube assembly 12 within the trachea 26, wherein the surface electrode 16 is illustrated as contacting the target tissue 28. In some instances, the diagram 49 of the ET tube assembly 12 within the trachea 26 may be omitted from the first indicator 48.

In FIGS. 6A-6E, the numerical indicator 51 includes a number corresponding to the amount of pressure between the surface electrode 16 and the target tissue 28 at two regions of the outer circumferential surface S, a first region 16a and a second region 16b, which are labeled on the diagram 49. In such an instance, the pressure sensor assembly 18 may be configured to sense the amount of pressure between the surface electrode 16 and the target tissue 28 at the first region 16a and the second region 16b. The first region 16a and the second region 16b may correspond to the previously described regions Ra, Rb, Rc, and Rd, which are shown in FIG. 4B. For instance, in FIGS. 6A-6E, the first region 16a includes the regions Ra and Rb and the second region 16b includes the regions Rc and Rd. In such instances, the divider D1 from FIG. 4B may divide the first region 16a and the second region 16b, as shown in the diagram 49. In other instances, the pressure sensor assembly 18 may be configured to sense the amount of pressure at regions other than the first and second regions 16a and 16b. Accordingly, in such instances, the first indicator 48 may include a number corresponding to the amount of pressure at the regions other than the first and second regions 16a and 16b.

In FIGS. 6A-6E, the numerical indicator 51 includes a first number 51a and a second number 51b, which correspond to the amount of pressure between the surface electrode 16 and the target tissue 28 at the first region 16a and the second region 16b of the outer circumferential surface S, respectively. As shown, the numerical indicator 51 may be placed adjacent to the diagram 49 of the ET tube assembly 12 such the first number 51a is aligned with the first region 16a and the second number 51b is aligned with the second region 16b. Furthermore, the numerical indicator 51 is configured to output a "4", "5", or "6" if the amount of pressure sensed at the corresponding region is too high, suggesting that the position of the ET tube 14 should be adjusted to decrease the pressure between the region of the outer circumferential surface S and the surface electrode 16. Likewise, the numerical indicator 51 is configured to output a "0", "1", or "2" if the amount of pressure sensed at the corresponding region is too low, suggesting that the position of the ET tube 14 should be adjusted to increase the pressure between the region of the outer circumferential surface S and the surface electrode 16. As such, by outputting a number corresponding to the amount of pressure between the outer circumferential surface S and the first and second regions 16a and 16b, the first indicator 48 is configured to facilitate proper placement of the ET tube 14 in the trachea 26.

Figure 6A:
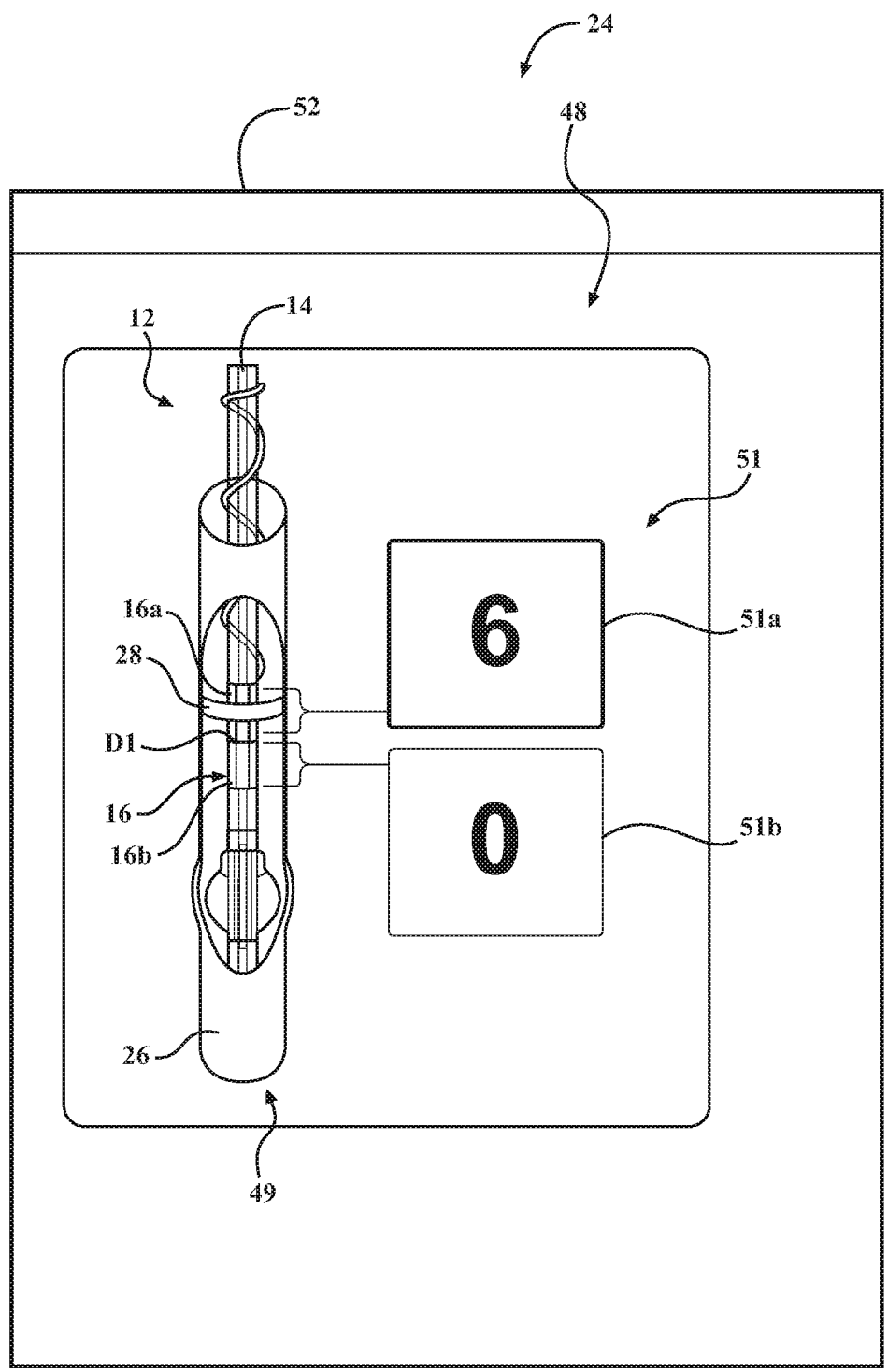
FIGS. 6A-6E are perspective views of examples of a first indicator output by the output device of the intraoperative nerve monitoring system where the first indicator includes a numerical indicator.

For example, in FIG. 6A, one instance where the numerical indicator 51 of the first indicator 48 facilitates proper placement of the ET tube 14 in the trachea 26 is shown. As shown, the numerical indicator 51 indicates that the amount of pressure between the surface electrode 16 and the target tissue 28 at the first region 16a is too high by outputting the number "6" as the first number 51a. Similarly, the numerical indicator 51 indicates that the amount of pressure at the second region 16b is too low by outputting the number "0" as the second number 51b. As such, the numerical indicator 51 suggests that the position of the ET tube 14 should be adjusted such that the amount of pressure is decreased at the first region 16a and increased at the second region 16b. As previously stated, the ET tube 14 may be inserted within the trachea 26 such that the ET tube 14 is rotatable clockwise and counterclockwise and slidable proximally and distally within the trachea 26, as illustrated by the directional arrows A1, A2, A3, and A4, respectively, in FIG. 4B. In the example of FIG. 6A, the numerical indicator 51 suggests that the ET tube 14 should be urged distally (along the direction of A4) in order to properly position the ET tube 14 within the trachea 26. In this way, the amount of pressure between the surface electrode 16 and the target tissue 28 is decreased at the first region 16a and the amount of pressure between the surface electrode 16 and the target tissue 28 is increased at the second region 16b.

For example, in FIG. 6A, one instance where the numerical indicator 51 of the first indicator 48 facilitates proper placement of the ET tube 14 in the trachea 26 is shown. As shown, the numerical indicator 51 indicates that the amount of pressure between the surface electrode 16 and the target tissue 28 at the first region 16a is too high by outputting the number "6" as the first number 51a. In addition, the first region 16a is highlighted in the diagram 49 and the first number 51a is highlighted. Similarly, the numerical indicator 51 indicates that the amount of pressure at the second region 16b is too low by outputting the number "0" as the second number 51b. As such, the numerical indicator 51 suggests that the position ET tube 14 should be adjusted such that the amount of pressure is decreased at the first region 16a and increased at the second region 16b. As previously stated, the ET tube 14 may be inserted within the trachea 26 such that the ET tube 14 is rotatable clockwise and counterclockwise and slidable proximally and distally within the trachea 26, as illustrated by the directional arrows A1, A2, A3, and A4, respectively, in FIG. 4B. In the example of FIG. 6A, the numerical indicator 51 suggests that the ET tube 14 should be urged distally along the direction of A4 in order to properly position the ET tube 14 within the trachea 26. In this way, the amount of pressure between the surface electrode 16 and the target tissue 28 is decreased at the first region 16a and the amount of pressure between the surface electrode 16 and the target tissue 28 is increased at the second region 16b.

Figure 6B:
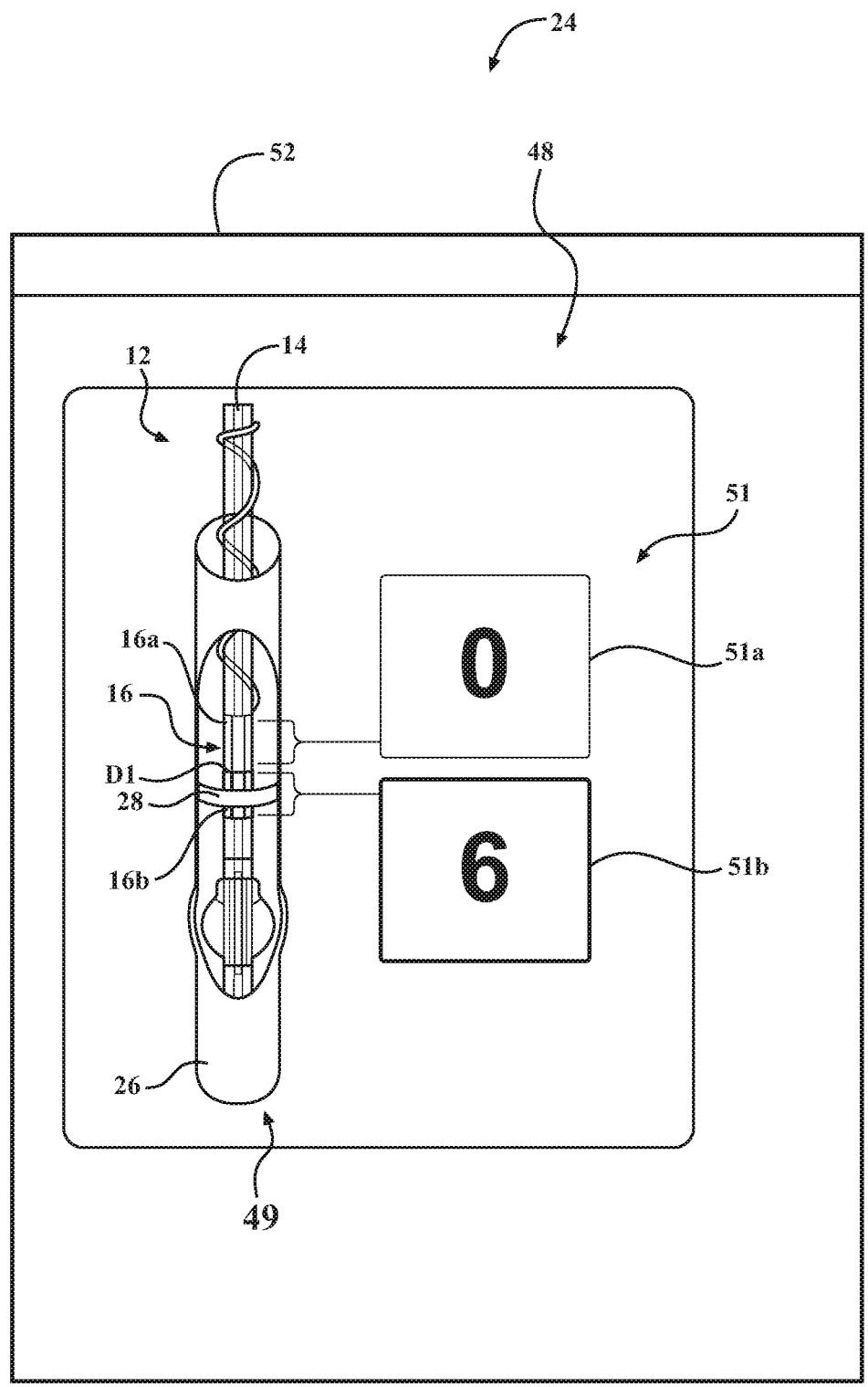

In FIG. 6B, another instance where the numerical indicator 51 of the first indicator 48 facilitates proper placement of the ET tube 14 in the trachea 26 is shown. As shown, the numerical indicator 51 indicates that the amount of pressure between the surface electrode 16 and the target tissue 28 at the first region 16a is too low by outputting the number "0" as the first number 51a. Similarly, the numerical indicator 51 indicates that the amount of pressure at the second region 16b is too high by outputting the number "6" as the second number 51b. In addition, the second region 16b is highlighted in the diagram 49 and the second number 51b is highlighted. As such, the numerical indicator 51 suggests that the position of the ET tube 14 should be adjusted such that the amount of pressure is increased at the first region 16a and decreased at the second region 16b. In the example of FIG. 6A, the numerical indicator 51 suggests that the ET tube 14 should be urged proximally along the direction of A3 in order to properly position the ET tube 14 within the trachea 26. In this way, the amount of pressure between the surface electrode 16 and the target tissue 28 is increased at the first region 16a and the amount of pressure between the surface electrode 16 and the target tissue 28 is decreased at the second region 16b.

Figure 6C:
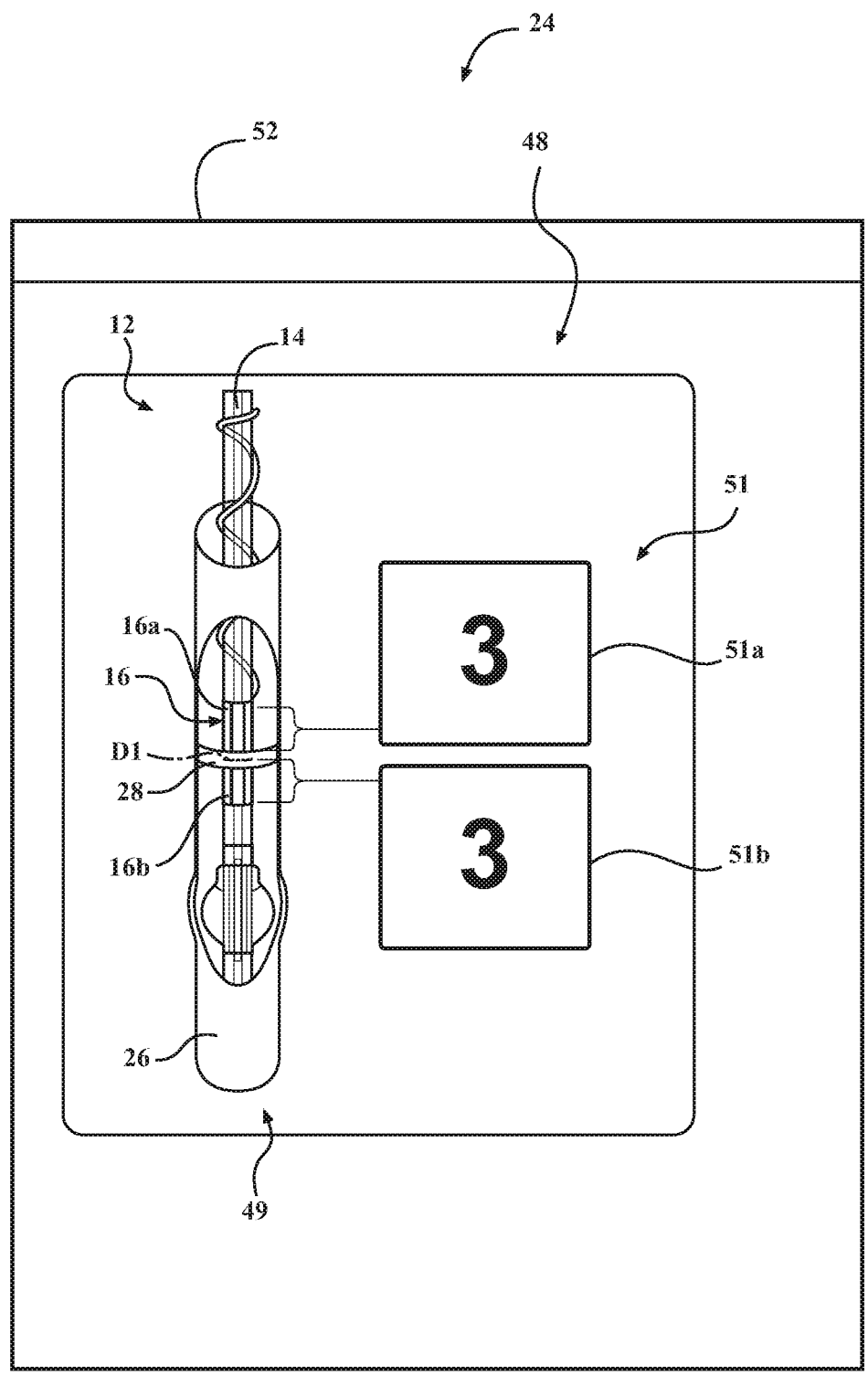

In FIG. 6C, an instance where the numerical indicator 51 of the first indicator 48 illustrates that the ET tube 14 is properly placed in the trachea 26 is shown. As shown, the numerical indicator 51 indicates that the amount of pressure at the first and second regions 16a and 16b is within a range of acceptability. As such, both the first region 16a and the second region 16b, which are divided by D1 (shown in the diagram 49 of FIG. 6C for illustrative purposes), are highlighted as shown in diagram 49. The first and second numbers 51a, 51b are also highlighted. As previously stated, each of the numbers 51a, 51b in FIGS. 6A-6E are scaled representations of a range of pressures. Here, the range of pressures may be selected such that the range corresponding to the number "3" is a range of acceptable pressures.

Figure 6D:
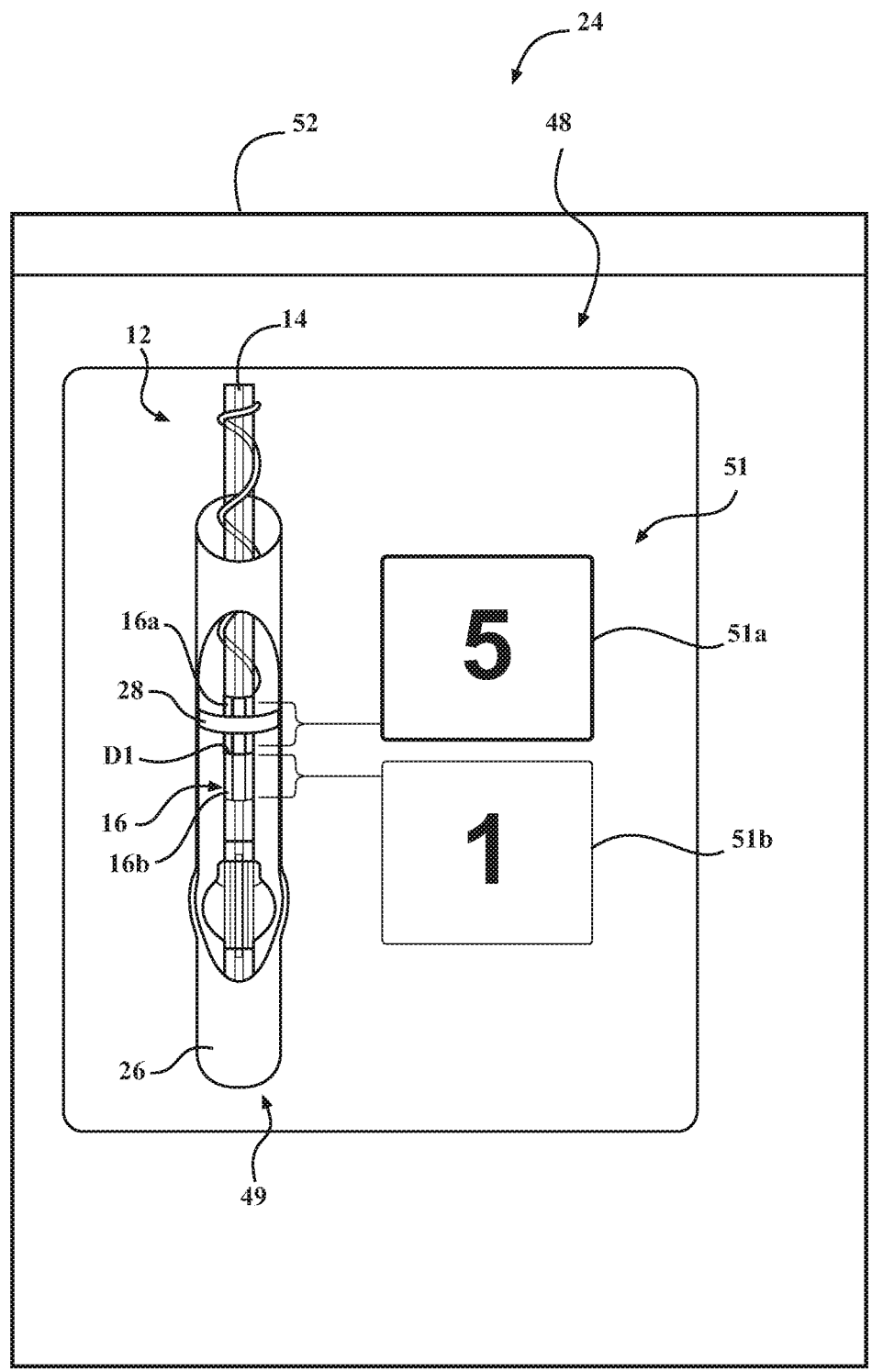
Figure 6E:
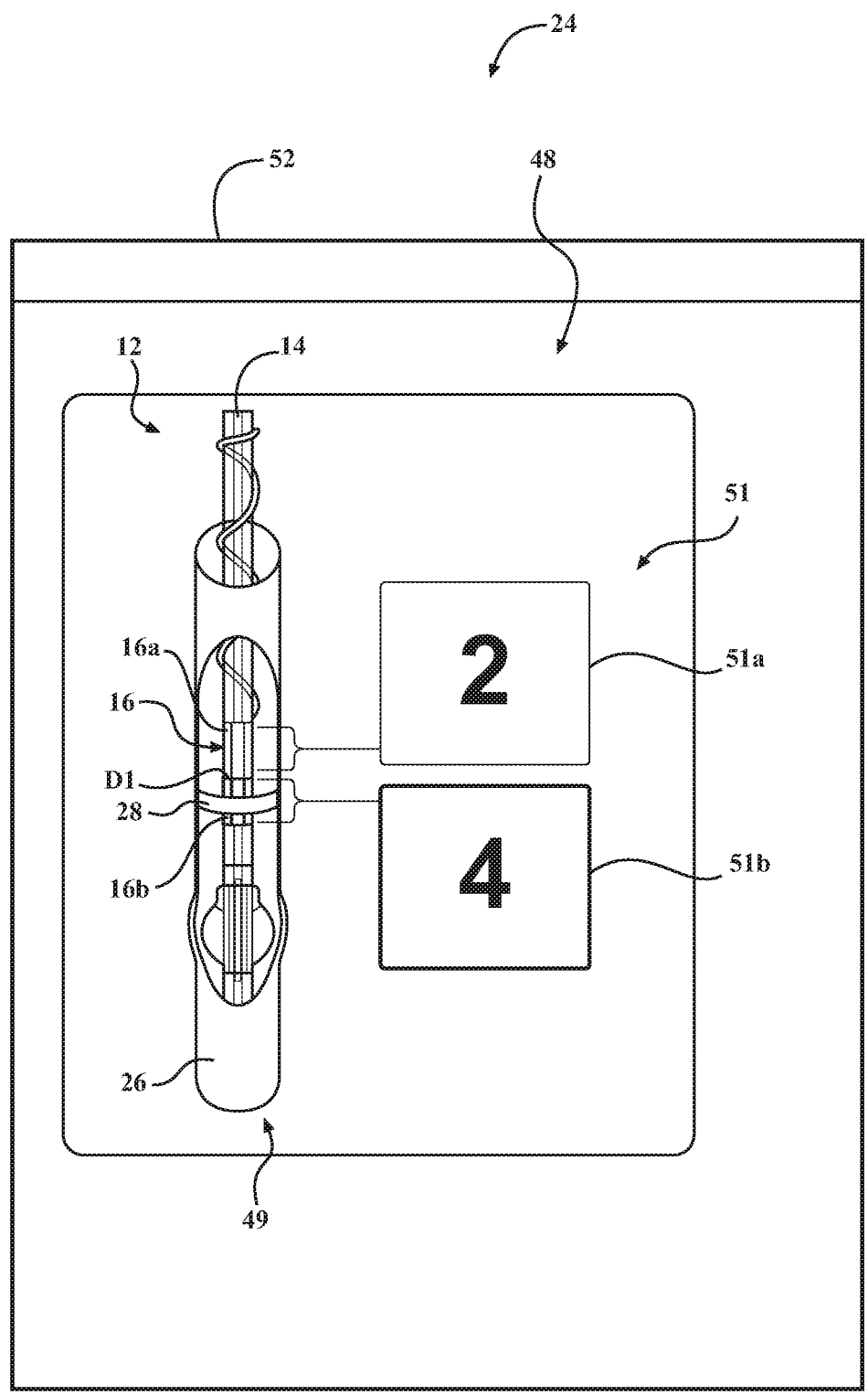

In FIGS. 6D and 6E, two more instances where the numerical indicator 51 of the first indicator 48 facilitates proper placement of the ET tube 14 in the trachea 26 are shown. Similar to FIGS. 6A and 6B, the numerical indicator 51 of FIGS. 6D and 6E indicates that the amount of pressure between the surface electrode 16 and the target tissue 28 is too high or too low at the first and second regions 16a and 16b. However, in FIG. 6D, the numerical indicator 51 outputs a "5" as the first number 51a and a "1" as the second number 51b, indicating that the amount of pressure is too high at the first region 16a and too low at the second region 16b. In FIG. 6E, the numerical indicator 51 outputs a "2" as the first number 51a and a "4" as the second number 51b, indicating that the amount of pressure is too low at the first region 16a and too high at the second region 16b. As previously stated, each of the numbers 51a, 51b in FIGS. 6A-6E are scaled representations of a range of pressures and each of the numbers from "0" to "6" correspond to an increasing range of pressures. In this way, the numerical indicator 51 indicates a magnitude by which the amount of pressure between the surface electrode 16 and the target tissue 28 is too high or too low and a magnitude of the suggested adjustment of the ET tube 14. For context, in some instances, after the output device 24 outputs the first indicator 48 of FIG. 6A, the output device 24 outputs the first indicator 48 of FIG. 6D as the ET tube 14 is urged distally along the direction of A4 before outputting the first indicator 48 of FIG. 6C. Similarly, after the output device 24 outputs the first indicator 48 of FIG. 6B, the output device 24 may output the first indicator 48 of FIG. 6E as the ET tube 14 is urged proximally along the direction of A3 before outputting the first indicator 48 of FIG. 6C.

In FIGS. 7A-7E, five examples of the first indicator 48 are shown. In each example, the first indicator 48 includes an indication of an adjustment 53 to correct the position of the ET tube 14 in the trachea 26. The indication of the adjustment 53 is based on the amount of pressure between the surface electrode 16 and the target tissue 28. Additionally, in FIGS. 7A-7E, the first indicator 48 is configured to provide the indication of the adjustment 53 based on the amount of pressure between the surface electrode 16 and the outer circumferential surface S at a plurality of regions. The plurality of regions may be the previously described regions Ra, Rb, Rc, and Rd. The first region 16a and the second region 16b, labelled in FIGS. 7A-7C, may include the regions Ra and Rb and the regions Rc and Rd, respectively. A third region 16c and a fourth region 16d, labelled in FIGS. 7C-7E, may include the regions Ra and Rc and the regions Rb and Rd, respectively.

Similar to the first indicator 48 of FIGS. 6A-6E, the first indicator 48 in FIGS. 7A-7E may include a diagram 49 of the ET tube assembly 12 within the trachea 26, wherein the surface electrode 16 is illustrated as contacting the target tissue 28. As previously stated, the diagram 49 of the ET tube assembly 12 within the trachea 26 may be omitted from the first indicator 48.

In FIGS. 7A-7E, the indication of the adjustment 53 includes an indication of a clockwise rotation A1 of the ET tube 14, a counterclockwise rotation A2 of the ET tube 14, a proximal sliding A3 of the ET tube 14, and a distal sliding A4 of the ET tube 14. However, in other instances, the indication of the adjustment 53 may omit any of the above adjustments. For example, the indications of the adjustments 53 in FIGS. 8A-8C only include a proximal sliding A3 of the ET tube 14, and a distal sliding A4 of the ET tube 14. Furthermore, while the indication of the adjustment 53 only includes an indication of one of the adjustments A1, A2, A3, and A4 at a time, in other instances, the indication of the adjustment 53 may include more than one adjustment A1, A2, A3, and A4. For example, the indication of the adjustment 53 may simultaneously include an indication of a clockwise rotation A1 and a distal sliding A4 of the ET tube 14.

Figure 7A:
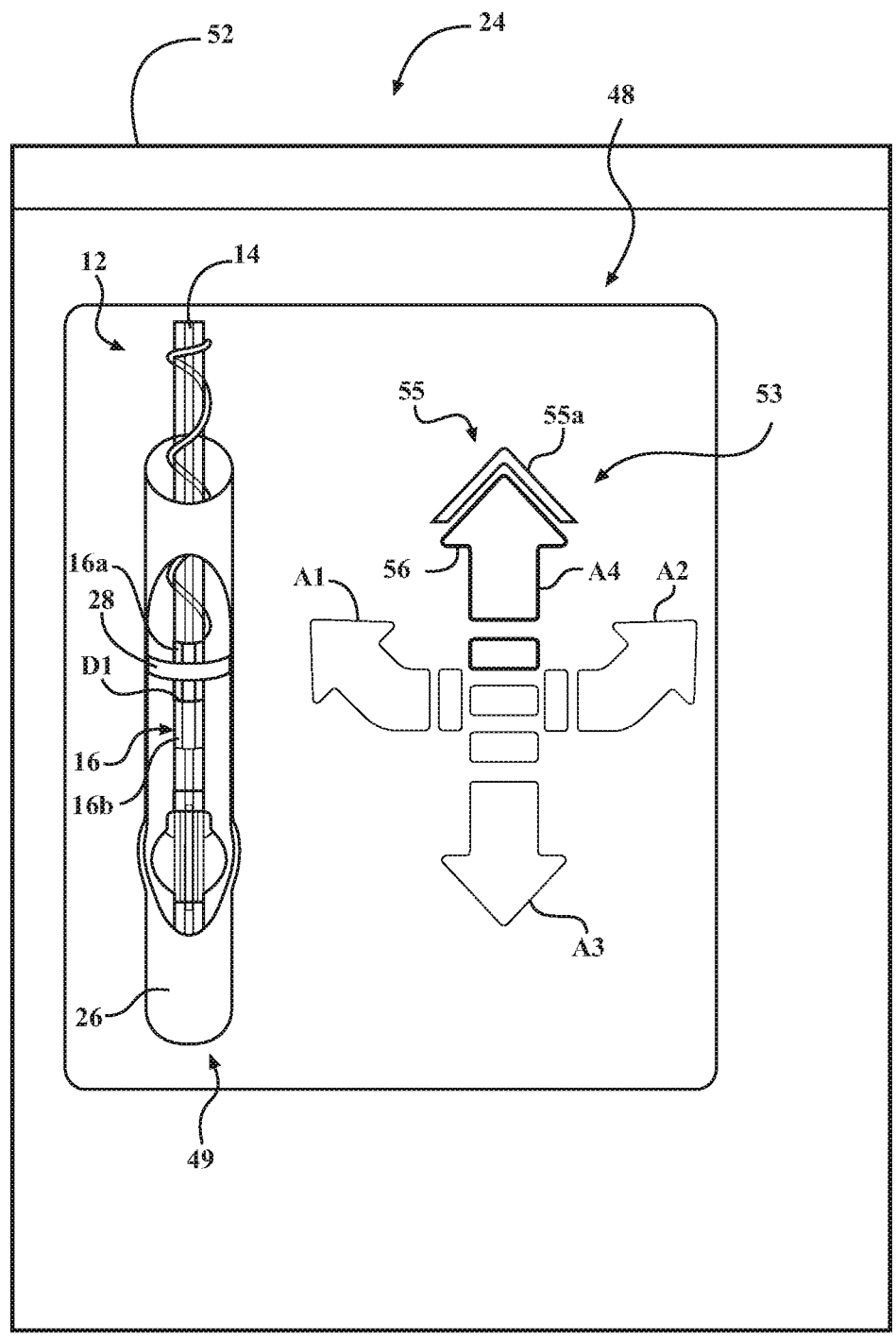
FIGS. 7A-7E are perspective views of examples of the first indicator where the first indicator includes an indication of an adjustment.

FIG. 7A illustrates an instance of the first indicator 48, where the indication of the adjustment 53 includes an indication of a distal sliding A4 of the ET tube 14. As previously stated, the indication of the adjustment 53 is based on the amount of pressure between the surface electrode 16 and the target tissue 28 at a plurality of regions. In FIG. 7A, the amount of pressure at the first region 16a is determined to be too high and the first region 16a is highlighted in the diagram 49. As such, the indication of the adjustment 53 is an indication of the distal sliding A4 of the ET tube 14 to decrease the amount of pressure at the first region 16a.

Figure 7B:
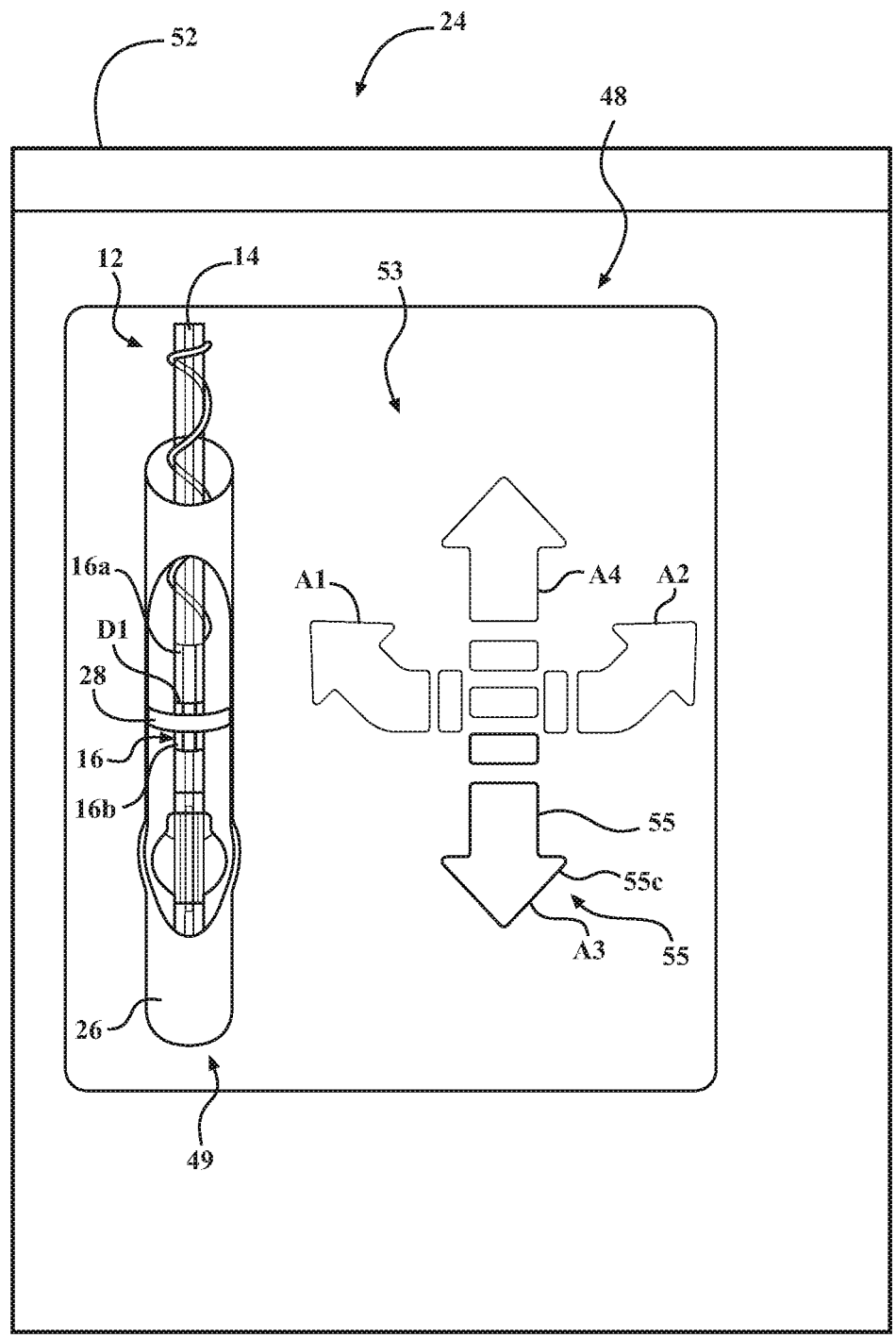

FIG. 7B illustrates an instance of the first indicator 48, where the indication of the adjustment 53 includes an indication of a proximal sliding A3 of the ET tube 14. In FIG. 7B, the amount of pressure at the second region 16b is determined to be too high and the second region 16b is highlighted in the diagram 49. As such, the indication of the adjustment 53 is an indication of the distal sliding A4 of the ET tube 14 to decrease the amount of pressure at the second region 16b.

The indications of the adjustments 53 in FIGS. 7A-7E include a magnitude indicator 55. Elements of the magnitude indicators 55 are labelled in FIGS. 7A and 7B for the purposes of explanation. In FIG. 7A, the magnitude indicator 55 includes a partial arrowhead 55a and a strong highlighting 55b of the distal sliding A4 adjustment to indicate a magnitude of the distal sliding A4 of the ET tube 14. In FIG. 7B, the magnitude indicator 55 does not include the partial arrowhead 55a and does not include the strong highlighting 55b. However, the magnitude indicator 55 in FIG. 7B includes a light highlighting 55c of the proximal sliding A3 adjustment. In this way, the magnitude indicator 55 indicates a magnitude of the proximal sliding A3 of the ET tube 14 that is lesser than the magnitude of the distal sliding A4 of the ET tube 14 in FIG. 7A. In other words, the magnitude indicators 55 in FIGS. 7A and 7B indicate that the ET tube 14 should be urged distally a farther distance in FIG. 7A than the ET tube 14 should be urged proximally in FIG. 7B.

Figure 7C:
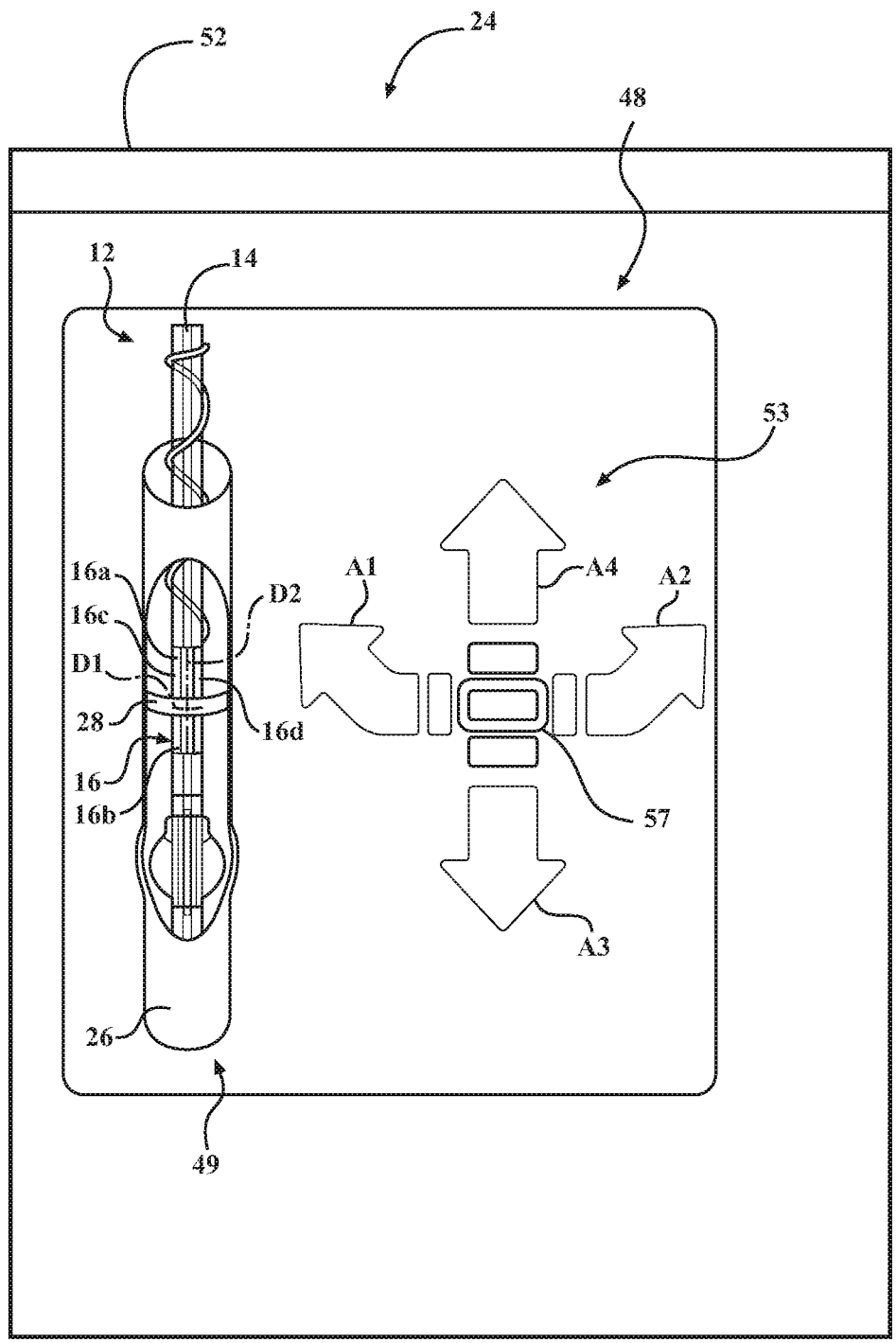

In FIG. 7C, an instance of the first indicator 48 is shown, where the indication of the adjustment 53 illustrates that the ET tube 14 is properly placed in the trachea 26 and no adjustment is required. In FIG. 7C, the first region 16a and the second region 16b of the ET tube 14, which are divided by D1 (shown in the diagram 49 of FIG. 7C for illustrative purposes), are highlighted as shown in diagram 49. In addition, the indication of the adjustment 53 includes an indication of proper placement 57.

Figure 7D:
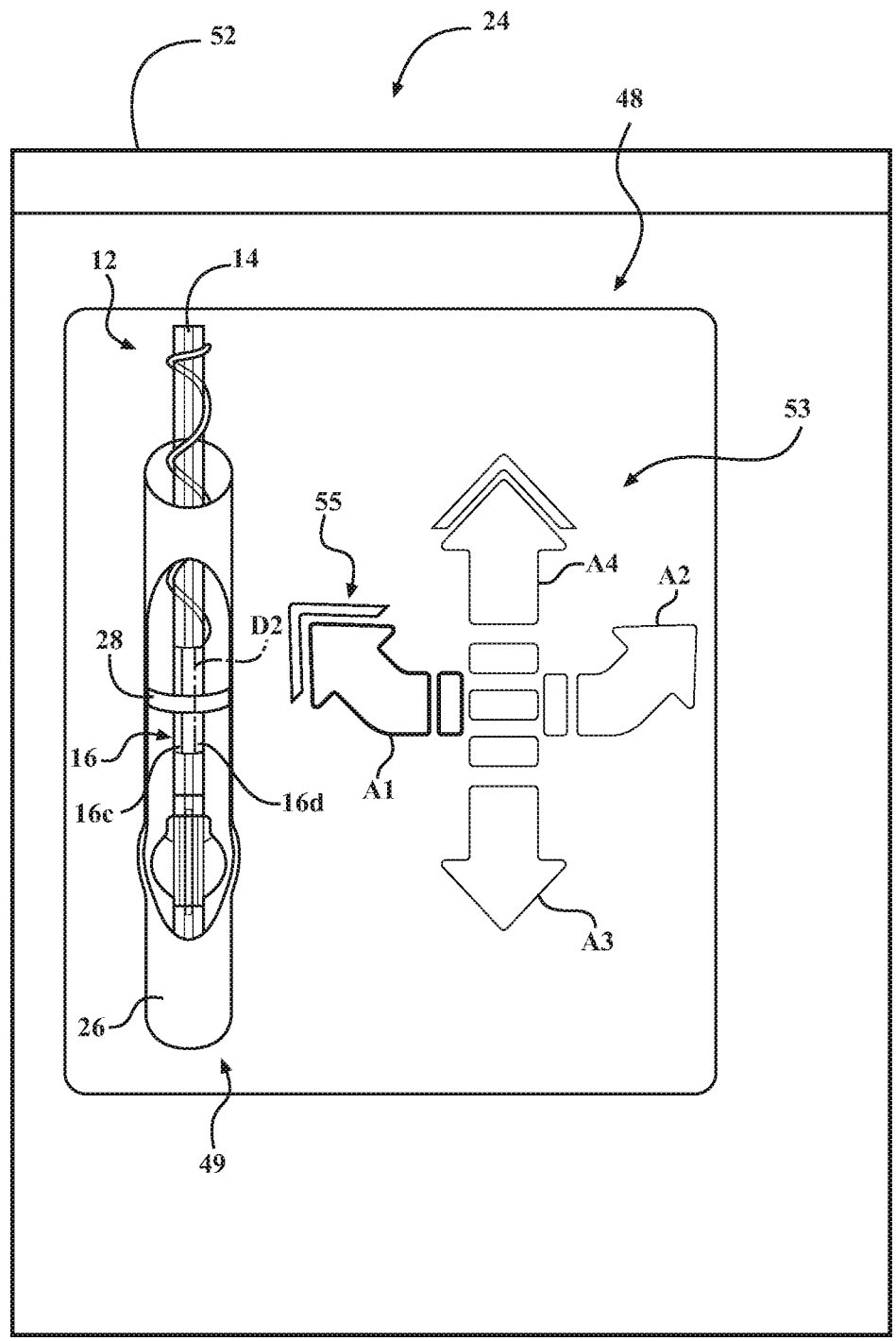
Figure 7E:
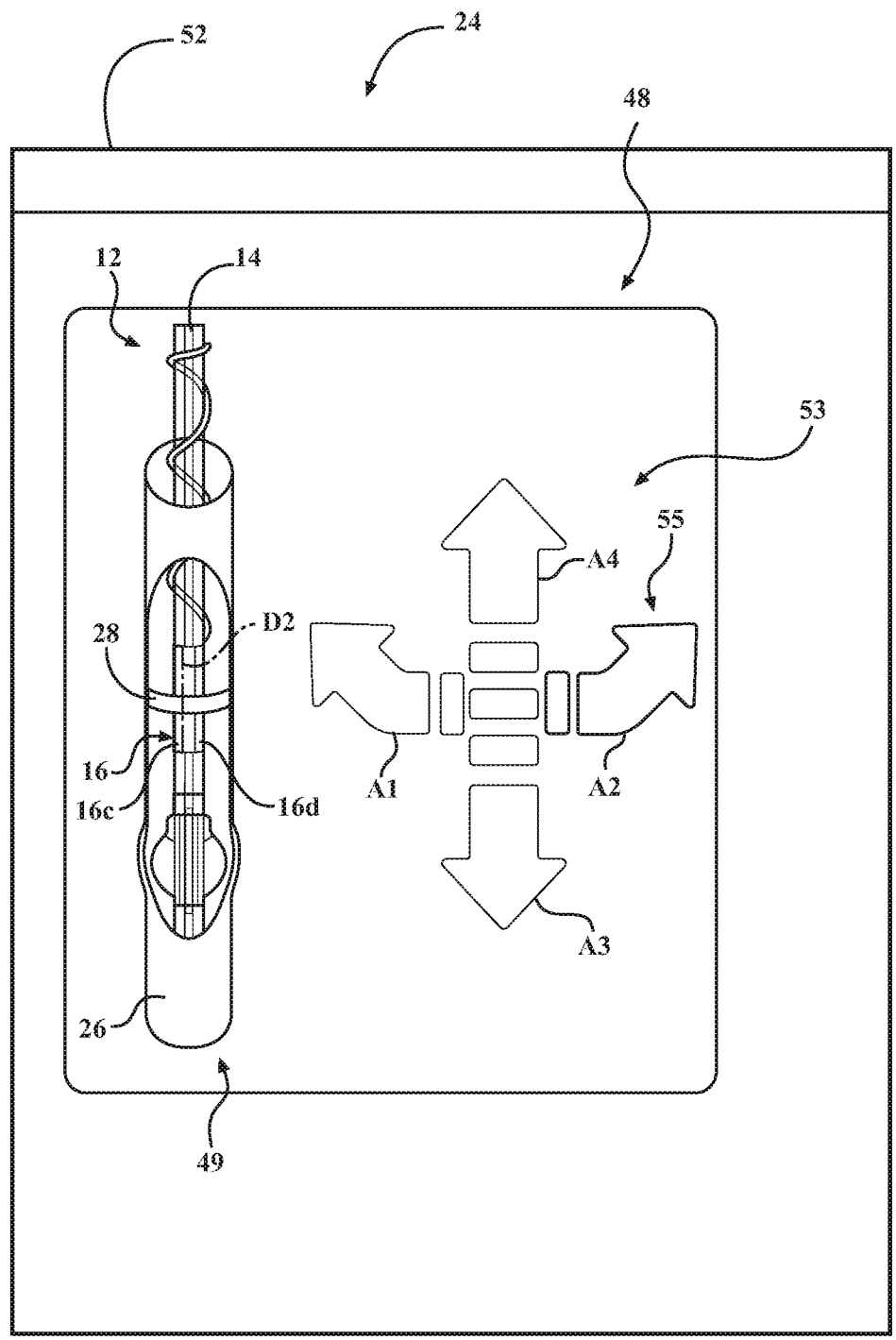

FIGS. 7D and 7E illustrate instances of the first indicator 48, where the indication of the adjustment 53 includes an indication of a clockwise rotation A1 of the ET tube 14 in FIG. 7D and an indication of a counterclockwise rotation A2 in FIG. 7E. In FIGS. 7D and 7E, the indication of the adjustment 53 is based on the amount of pressure at the third region 16c and the fourth region 16d, which are divided by divider D2 (the divider is shown in FIGS. 7C-7E for illustrative purposes). In FIG. 7D, the amount of pressure at the third region 16c is determined to be too high and the third region 16c is highlighted in the diagram 49. In FIG. 7E, the amount of pressure at the fourth region 16d is determined to be too high and the fourth region 16d is highlighted in the diagram 49. Furthermore, referring back to FIG. 7C, where the indication of the adjustment 53 illustrates that no adjustment to the ET tube 14 is required, the divider D2 is illustrated as bisecting the surface electrode 16 vertically. Accordingly, in FIGS. 7D and 7E, where the indication of the adjustment 53 indicates that the ET tube 14 should be rotated clockwise A1 and counterclockwise A2, the divider D2 is horizontally offset. Additionally, the indication of the adjustment 53 of FIGS. 7D and 7E includes the magnitude indicator 55. As such, the ET tube 14 should be rotated clockwise A1 a farther distance in FIG. 7D than the ET tube 14 should be rotated counterclockwise A2 in FIG. 7E.

In FIGS. 6A-7E, several examples of the first indicator 48 are shown. However, in other instances, the first indicator 48 may vary. For instance, the first indicator 48 may include color-coding, which may include any suitable color. In one such instance, the highlighted regions of the surface electrode 16, as shown in the diagram 49, may be highlighted with a bright red when the amount of pressure at the region is too high and the ET tube 14 requires an adjustment. The highlighted regions of the surface electrode 16 may be highlighted with a dull green when the ET tube 14 is properly placed. Similarly, the numbers 51a, 51b and the adjustments 53 in the A1, A2, A3, A4 directions may be highlighted bright red when the ET tube 14 requires an adjustment and the numerical indicator 51 and the indication of proper placement 57 may be highlighted dull green when the ET tube is properly placed. In another instance, elements of the first indicator 48, such as the diagram 49, the numerical indicator 51, and the indicator of the adjustment 53 may not be highlighted. In yet another instance, a size and a position of the elements of the first indicator 48 may vary.

Figure 8A:
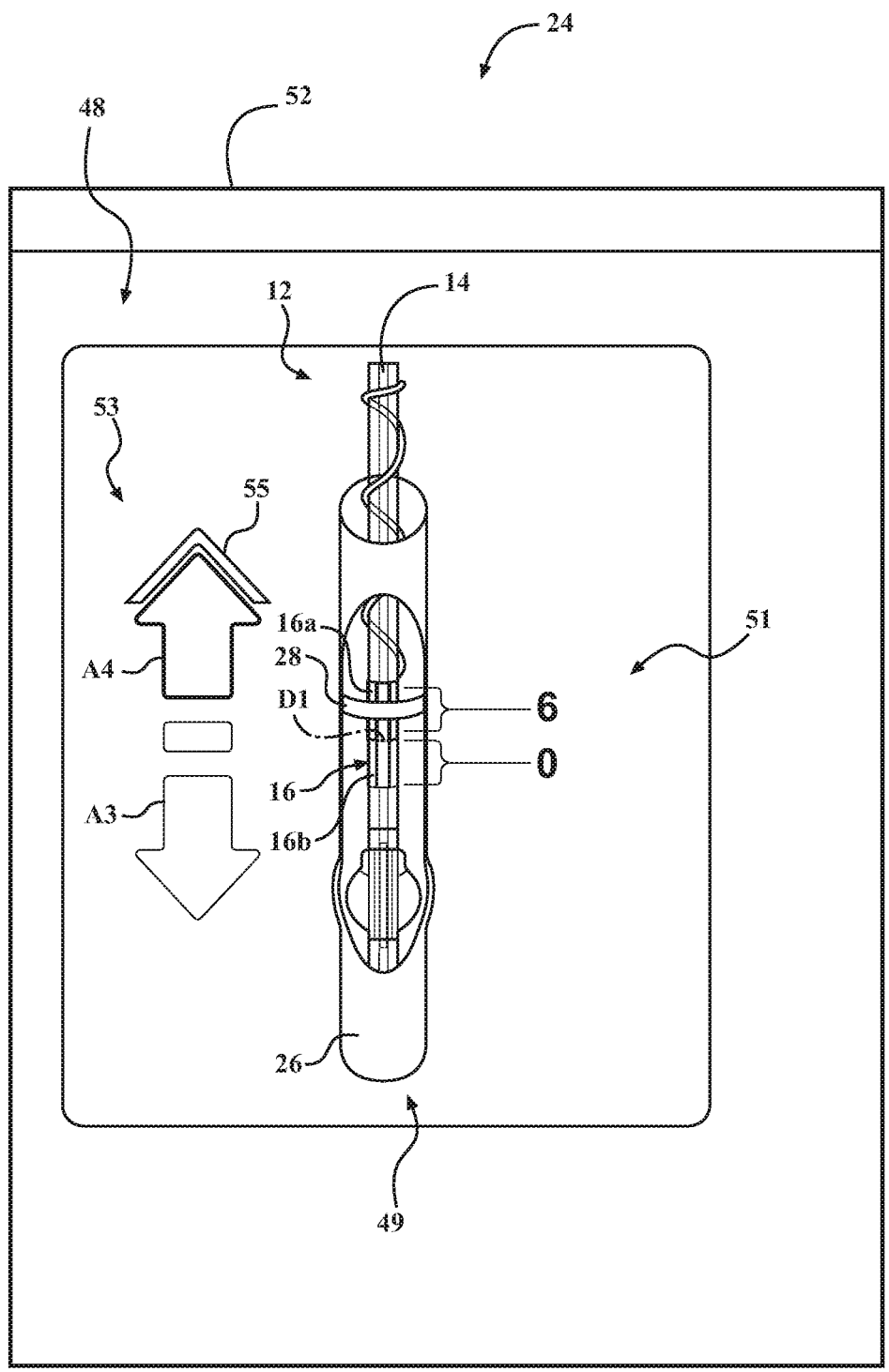
FIGS. 8A-8C are perspective views of examples of the first indicator where the first indicator includes the numerical indicator and the indication of an adjustment.
Figure 8B:
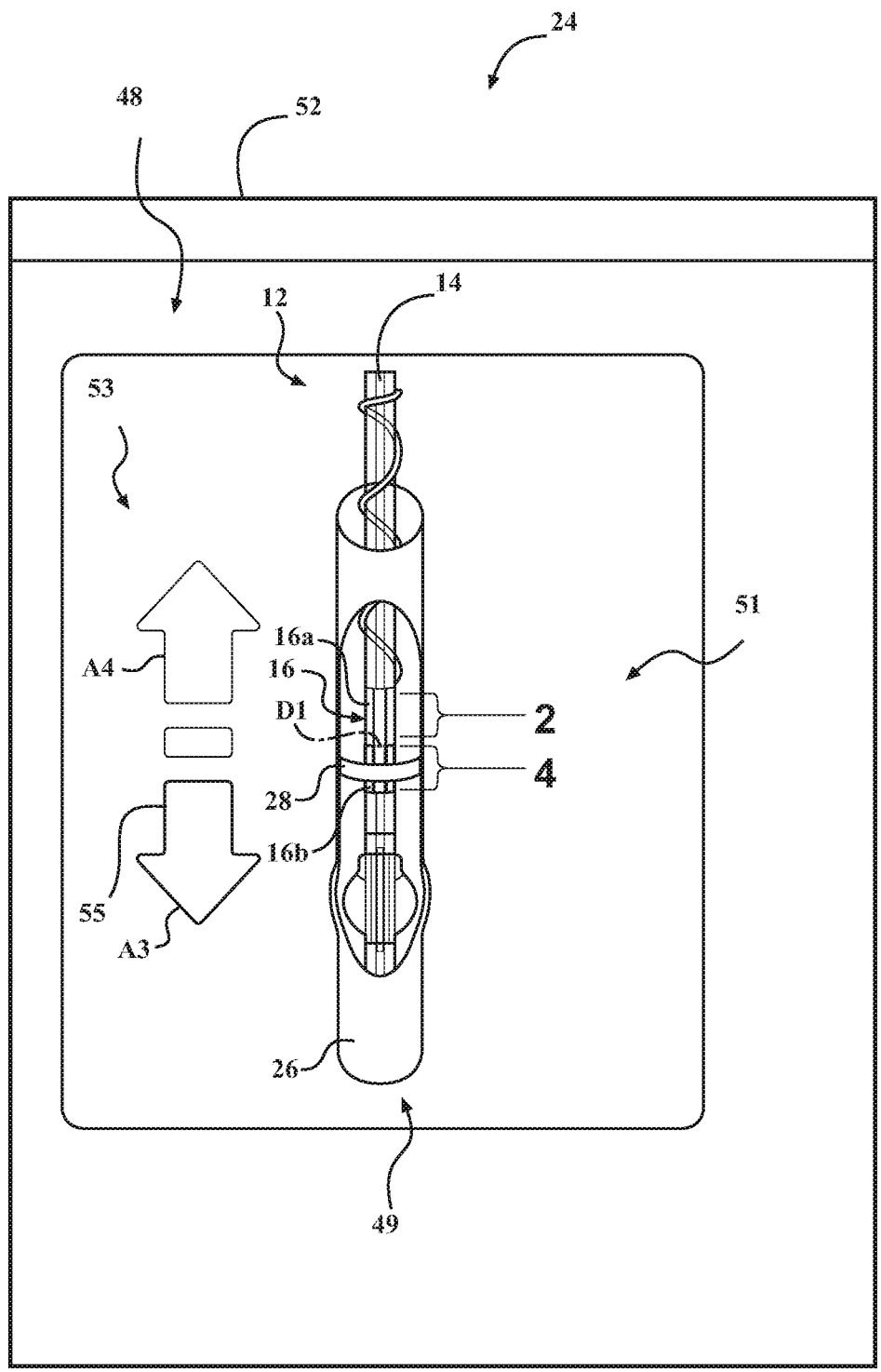
Figure 8C:
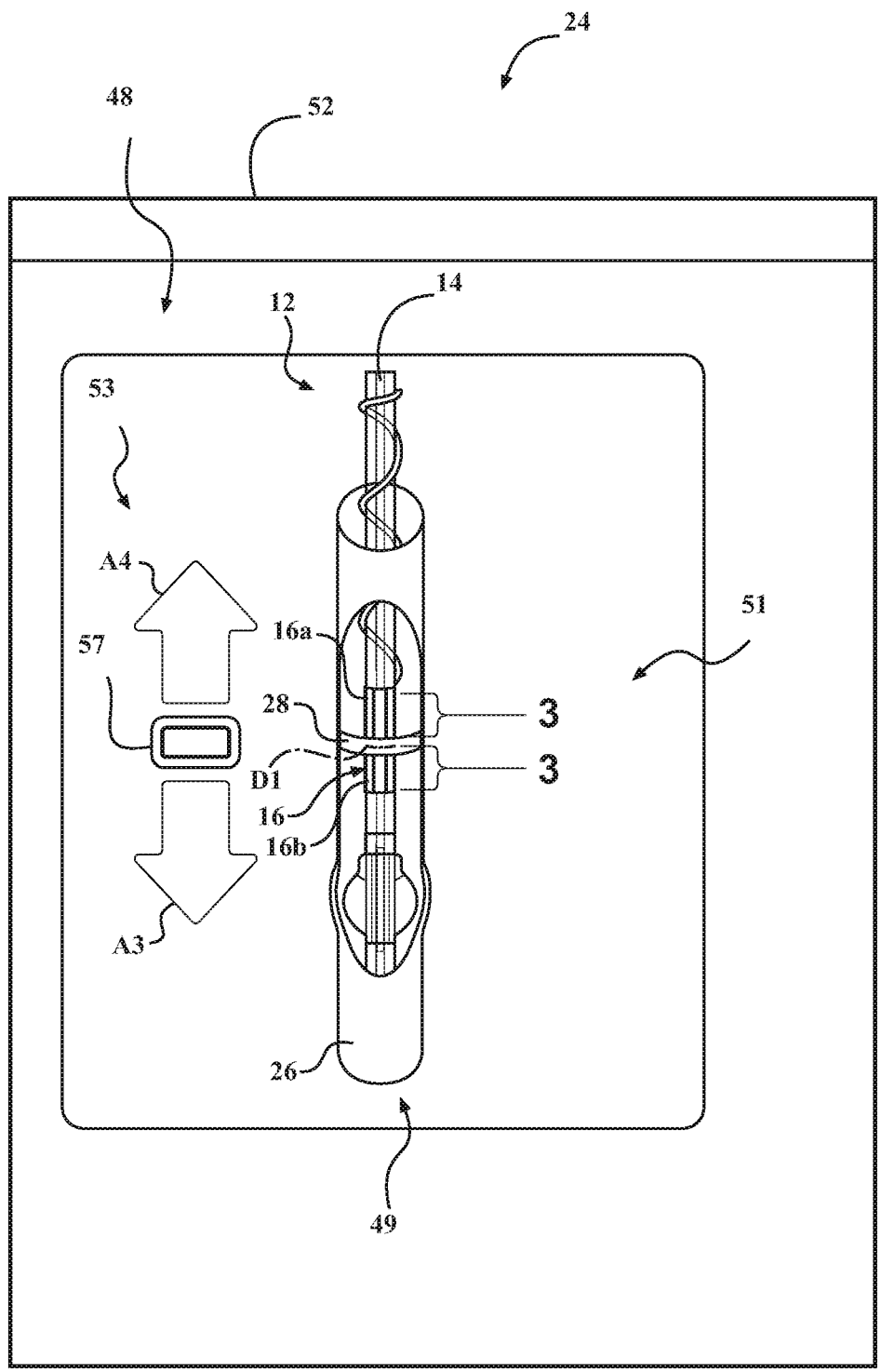

In some instances, such as the examples of the first indicator 48 shown in FIGS. 8A-8C, the first indicator 48 may include the numerical indicator 51 and the indicator of the adjustment 53. As shown in FIG. 8A, the numerical indicator 51 and the diagram 49 indicate that the amount of pressure in the first region 16a is too high. Accordingly, the indication of the adjustment 53 indicates that the ET tube 14 should be distally urged A4. In FIG. 8B, the numerical indicator 51 and the diagram 49 indicate that the amount of pressure in the second region 16b is too high. Accordingly, the indication of the adjustment 53 indicates that the ET tube 14 should be proximally urged A3. In FIG. 8C, the numerical indicator 51 and the diagram 49 indicate that the ET tube 14 is properly placed. Accordingly, the indication of the adjustment 53 includes the indication of proper placement 57.

Figure 9:
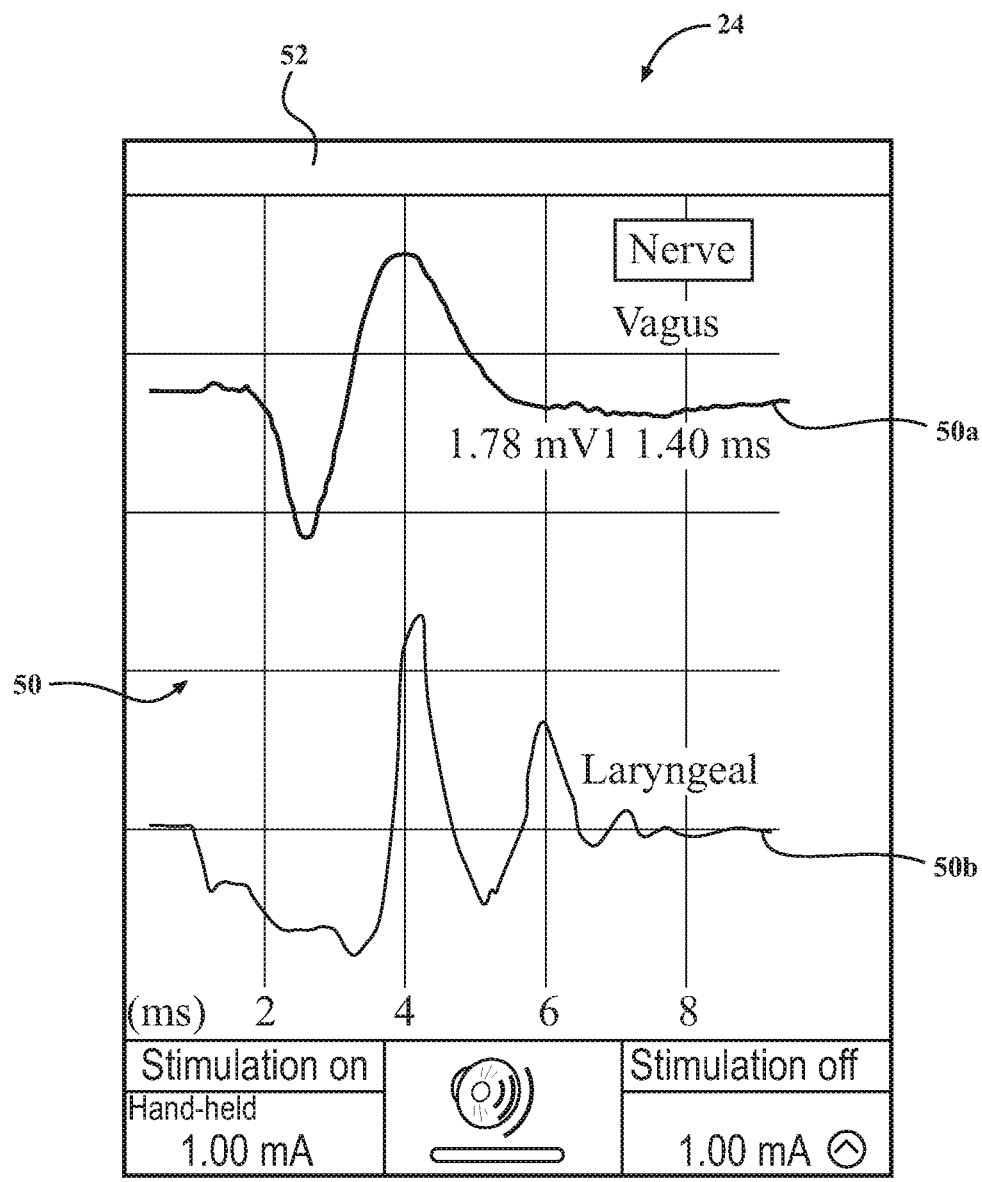
FIG. 9 is a perspective view of a second indicator output by the output device of the intraoperative nerve monitoring system.

In FIG. 9, an instance of the second indicator 50 is shown, wherein the second indicator 50 includes a waveform corresponding to the nerve activity monitored by the surface electrode 16. In the instance of FIG. 9, the surface electrode 16 is configured to monitor nerve activity of the valgus nerve 30 and the laryngeal nerve 31 (shown in FIG. 4A). As such, the second indicator 50 in FIG. 9 includes a waveform 50a corresponding to the monitored activity of the valgus nerve 30 and a waveform 50b corresponding to the monitored activity of the laryngeal nerve 31. In instances where the surface electrode 16 is configured to monitor nerve activity of a different nerve, the second indicator 50 may include a waveform corresponding to the nerve activity of the different nerve. Furthermore, as previously stated, the surface electrode 16 may be configured to monitor the nerve activity of any number of nerves. Accordingly, the second indicator 50 may include any number of corresponding waveforms.

Figure 10:
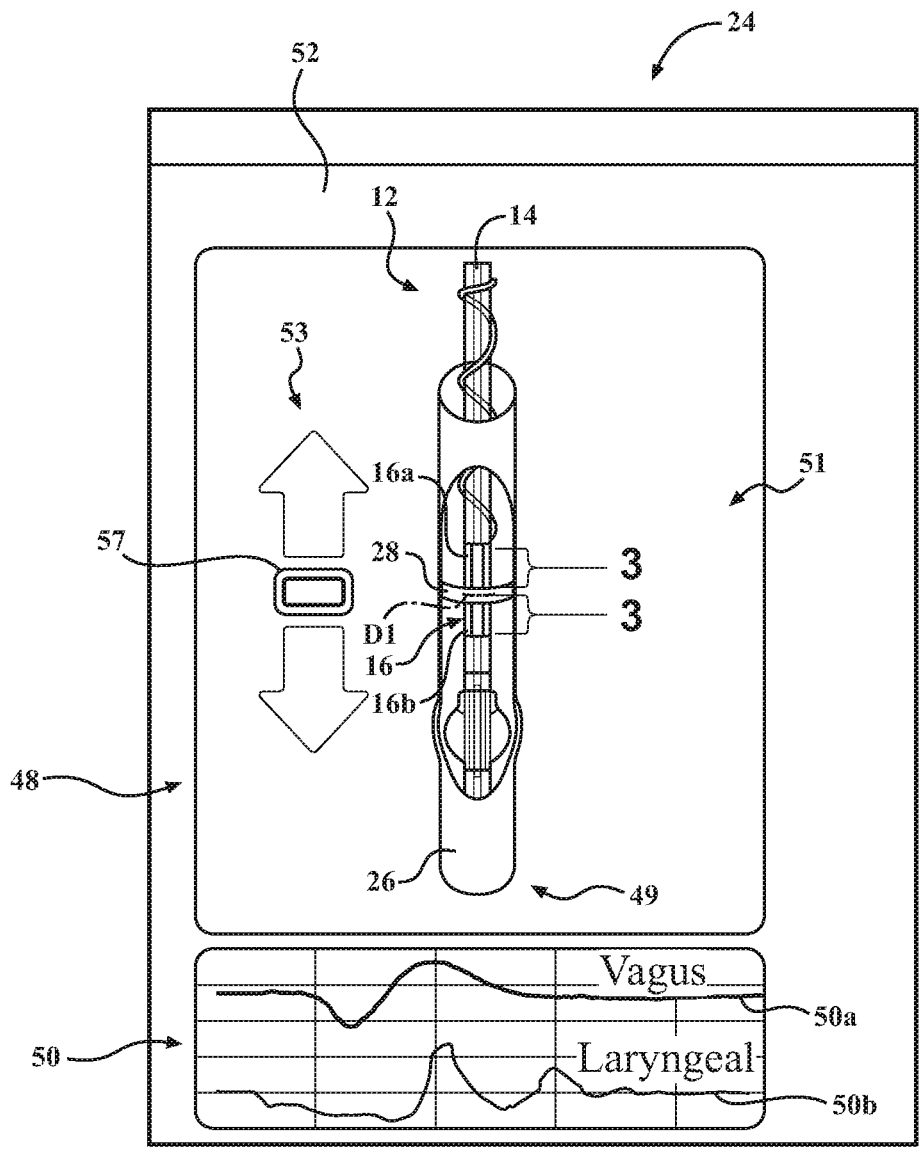
FIG. 10 is a perspective view of the output device where the output device outputs the first indicator and the second indicator.

In FIG. 10, an instance of the output device 24 is shown, wherein the output device 24 is configured to output the first indicator 48 and the second indicator 50 concurrently. In FIG. 10, the output device 24 outputs an instance of the first indicator 48 where the first indicator 48 includes the numerical indicator 51 and the indication of the adjustment 53. The output device 24 also outputs an instance of the second indicator 50, where the second indicator 50 includes the waveform 50a corresponding to the monitored activity of the valgus nerve 30 and the waveform 50b corresponding to the monitored activity of the laryngeal nerve 31. In other instances, the output device 24 may output any previously described instance of the first indicator 48 or any combination thereof. Similarly, the output device 24 may concurrently output any previously described instance of the second indicator 50 or any combinations thereof.

Figure 3A:
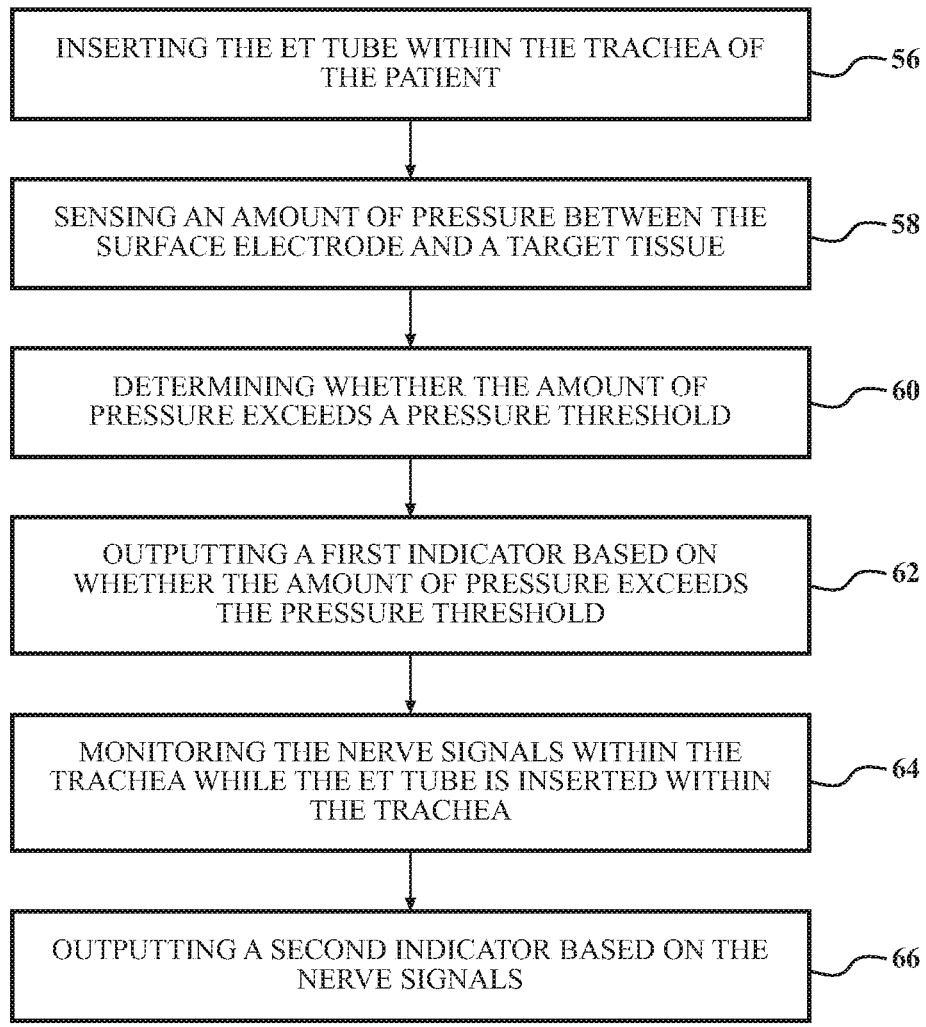
FIG. 3A is a flowchart of a method of operating the intraoperative nerve monitoring system.

Referring now to FIG. 3A, a method of operating the intraoperative nerve monitoring system 10 is shown. The method includes a step 56 of inserting the ET tube 14 within the trachea 26 of the patient; a step 58 of sensing, with the pressure sensor assembly 18, an amount of pressure between the surface electrode 16 and a target tissue 28; a step 60 of determining, with the controller 22, whether the amount of pressure exceeds a pressure threshold; a step 62 of outputting, with the output device 24, the first indicator 48 based on whether the amount of pressure exceeds the pressure threshold to facilitate proper placement of the ET tube in the trachea; a step 64 of monitoring, with the surface electrode 16, the nerve activity within the trachea 26 while the ET tube 14 is inserted within the trachea 26; and a step 66 of outputting, with the output device 24, a second indicator 50 based on the nerve activity. While the steps 56-66 of the method are shown as proceeding in a particular order in FIG. 3A, the steps of any method described herein may be ordered in any suitable order.

The step 56 of inserting the ET tube 14 within the trachea 26 is illustrated in FIG. 4A. As shown, and as previously described, the ET tube 14 is at least partially inserted within the trachea 26. The step 58 of sensing, with the pressure sensor assembly 18, the amount of pressure between the surface electrode 16 and the target tissue 28 is shown in FIG. 4B. As shown, and as previously described, the target tissue 28 is the laryngeal muscle 28. The step 64 of monitoring, with the surface electrode 16, nerve activity within the trachea 26 is shown in FIG. 4A. As shown and as previously described, the surface electrode 16 is configured to monitor the nerve activity of the valgus nerve 30 and the laryngeal nerve 31.

Figure 5:
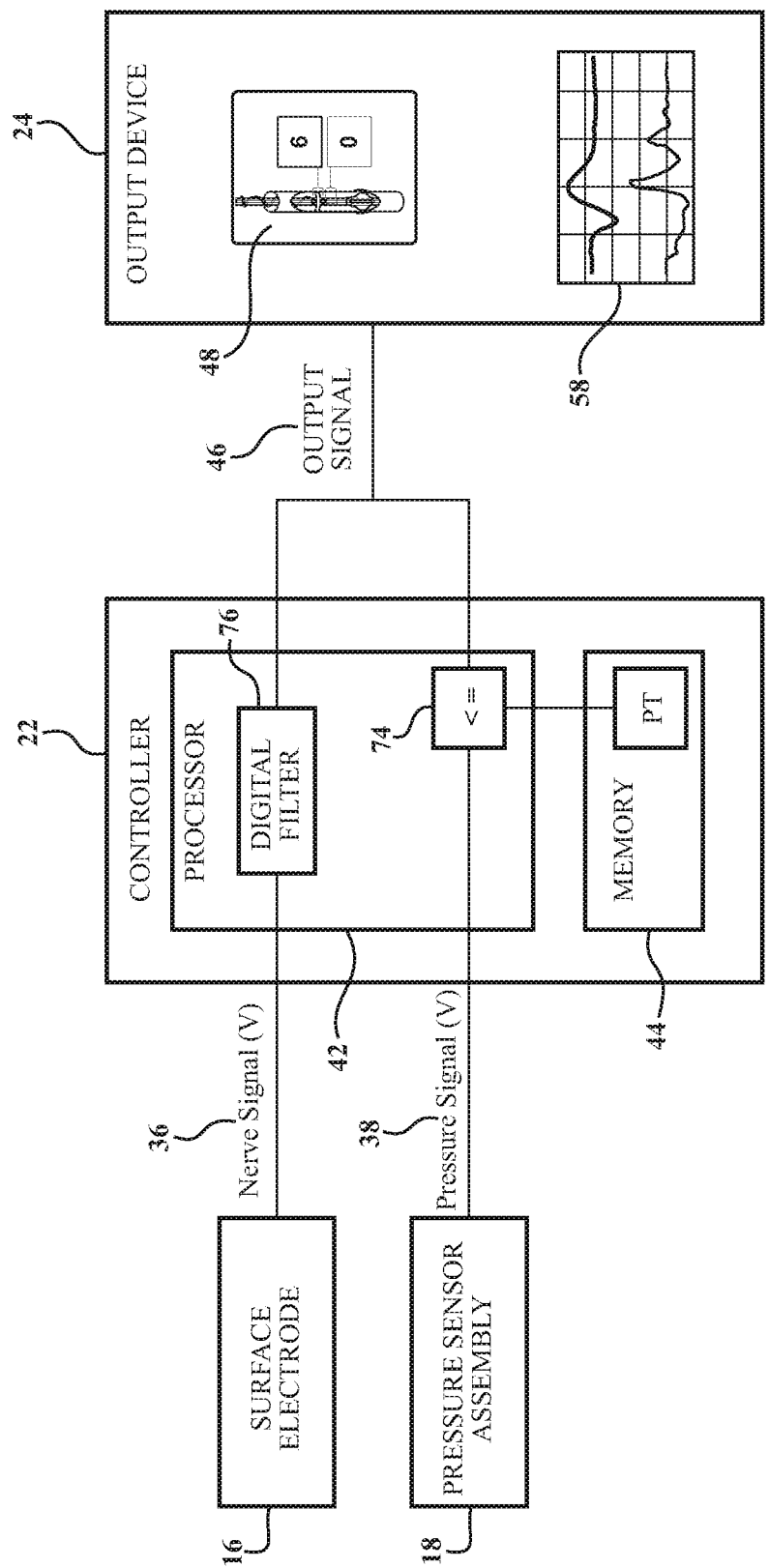
FIG. 5 is a schematic view of the surface electrode, the pressure sensor assembly, a controller, and an output device of the intraoperative nerve monitoring system.

FIG. 5 illustrates the step 60 of determining whether the amount of pressure between the surface electrode 16 and the target tissue 28 exceeds a pressure threshold. In the instance of FIG. 5, the processor 42 of the controller 22 receives the pressure signal 38 from the pressure sensor assembly 18, which corresponds to the amount of pressure, and compares the pressure signal 38, using a comparator 74, to a pressure threshold PT value stored in the memory 44 of the controller 22. The controller 22 then outputs the output signal 46 to the output device 24. In other instances, the controller 22 may perform step 60 using different components. For example, the controller 22 may perform step 60 without the comparator 74, or may substitute the comparator 74 for any other device suitable for comparing the pressure signal 38 to the pressure threshold PT, such as a microprocessor. Additionally, the controller 22 may perform step 60 without the use of the processor 42 and/or the memory 44.

In other instances, the controller 22 may determine whether the amount of pressure between the surface electrode 16 and the target tissue 28 falls within a pressure range. For example, in some instances, such as the examples of the first indicator 48 shown in FIGS. 6A-6E, the first indicator 48 may include a numerical indicator 48 configured to output a whole number based on the amount of pressure during step 62. Each of the whole numbers may correspond to a range of pressures. As such, during step 60, the controller 22 may determine which pressure range the amount of pressure falls within during step 60. For example, in FIGS. 6A-6E, the numerical indicator 48 outputs a number between "0" to "6", inclusive, during step 62. The numbers "0" to "6" corresponding to seven increasing ranges of pressure. As such, during step 60, the controller 22 may be configured to determine which of the seven ranges of pressure the amount of pressure falls within.

FIG. 5 also illustrates the step 62 of outputting the first indicator 48 and the step 66 of outputting the second indicator 50. As previously discussed, the controller 22 outputs the output signal 46 based on determining whether the amount of pressure between the surface electrode 16 and the target tissue 28 exceeds the pressure threshold PT. As shown in FIG. 5, the controller 22 may also output the output signal 46 based on the nerve signal 36, which corresponds to the nerve activity within the trachea 26. For example, in FIG. 5, the processor 42 filters the nerve signal 36 using the digital filter 76 before outputting the output signal 46. In this way, the controller 22 outputs the output signal 46 based on whether the amount of pressure exceeds the pressure threshold PT and based on the nerve activity. In other instances, the processor 42 may optionally omit the filtering of the nerve signal 36. Furthermore, the processor 42 may include other components for processing the nerve signal 36 received from the surface electrode 16. The controller 22 may also optionally omit any processing of the nerve signal 36.

After receiving the output signal, the output device 24 may output the first indicator 48 based on whether the amount of pressure between the surface electrode 16 and the target tissue 28 exceeds the pressure threshold PT during step 60. For example, in the instance of FIGS. 6C and 7C, the controller 22 may determine that the amount of pressure does not exceed the pressure threshold PT during step 60. As such, during step 62, the output device 24 may output the first indicator 48, which may include the numerical indicator 51 and the indication of the adjustment 53. In FIG. 6C, the numerical indicator 51 outputs a "3" for the first number 51a and the second number 51b, suggesting that the ET tube 14 is properly placed. In FIG. 7C, the indication of the adjustment 53 includes the indication of proper placement 57 to indicate that the ET tube 14 is properly placed.

After receiving the output signal 46, the output device 24 may also output the second indicator 50 based on the nerve activity during step 66. For example, referring to FIG. 9, the output device 24 may output the second indicator 50 based on the nerve activity sensed by the surface electrode 16. In FIG. 9, the output device 24 outputs the second indicator 50, which includes the waveform 50a of the nerve activity of the valgus nerve 30 and the waveform 50b of the nerve activity of the laryngeal nerve 31.

Figure 3B:
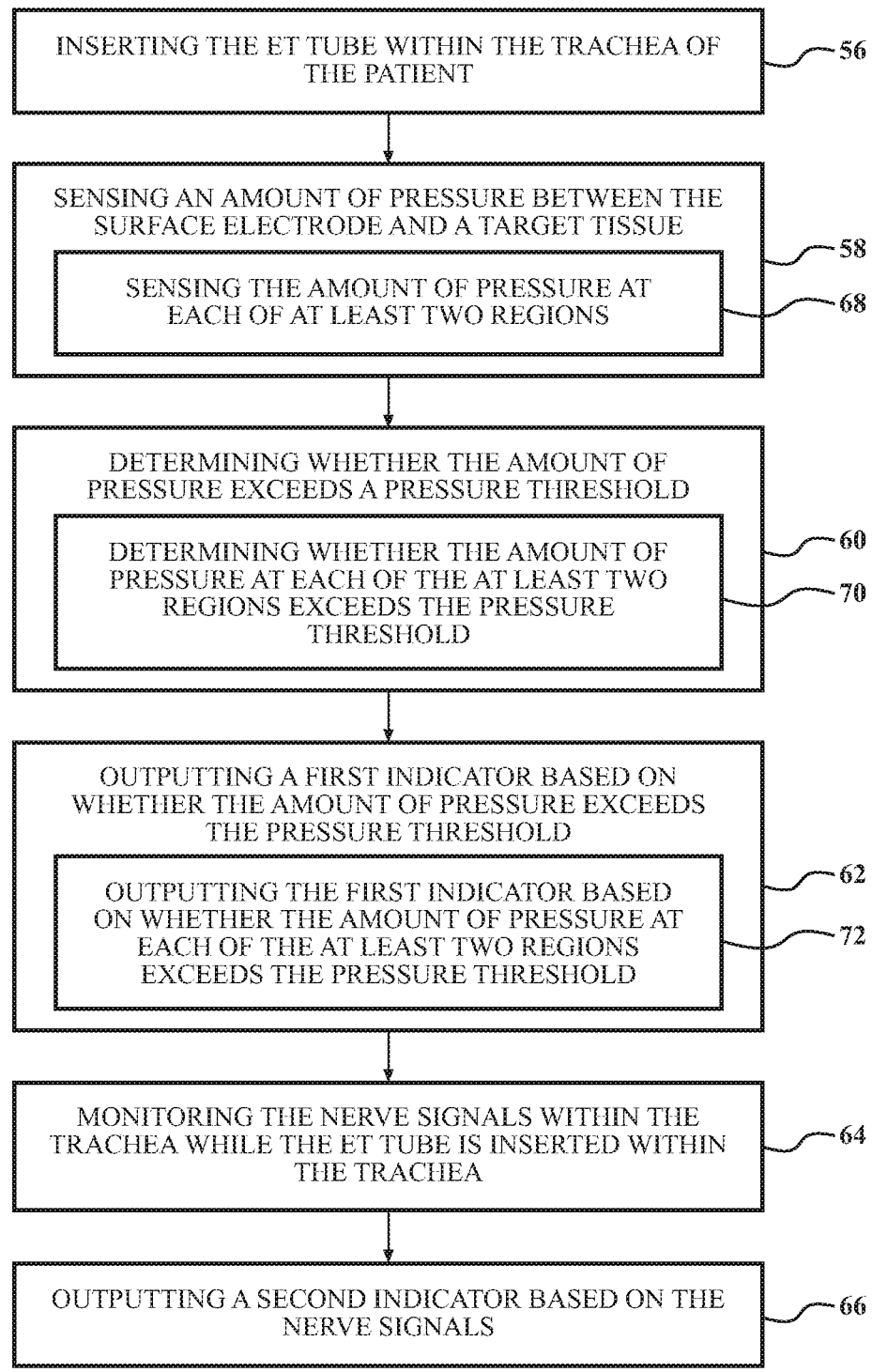
FIG. 3B is a flowchart of an instance of the method of operating the intraoperative nerve monitoring system.

FIG. 3B illustrates a second instance of the method, wherein the pressure sensor assembly 18 is configured to sense the amount of pressure between the surface electrode 16 and the target tissue 28 by sensing the amount of pressure between the surface electrode 16 and the target tissue 28 at each of at least two regions spaced apart from one another on the outer circumferential surface S. For example, referring to FIG. 4B, the at least two regions may be the four previously described regions Ra, Rb, Rc, and Rd. As such, while the method of FIG. 4B includes the previously described steps 56, 64, and 66, the method also includes instances of the previously described steps 58, 60, and 62, which are illustrated as steps 58', 60', and 62', and which include steps 68, 70, and 72, respectively, described below.

As shown in FIG. 3B, the step 58' includes the step 68 of sensing, with the pressure sensor assembly 18, the amount of pressure at each of at least two regions. Step 58' is further illustrated in FIG. 4B. As shown, the pressure sensor assembly 18 includes the pressure sensors 18a, 18b, 18c, and 18d, which are configured to sense the amount of pressure between the surface electrode 16 and the target tissue 28 at the regions Ra, Rb, Rc, and Rd, respectively.

Also shown in FIG. 3B, the step 60' includes the step 70 of determining, with the controller 22, whether the amount of pressure at each of the at least two regions exceeds the pressure threshold PT. For example, referring to FIG. 5, the pressure signal 38 may include the amount of pressure at each of the regions Ra, Rb, Rc, and Rd of FIG. 4B. The processor 42 may then determine whether the amount of pressure at each of the regions Ra, Rb, Rc, and Rd exceeds the pressure threshold PT before outputting the output signal 46. In such an instance, where the controller 22 determines whether the amount of pressure at a plurality of regions exceeds the pressure threshold PT, the pressure threshold PT may be an array stored in the memory 44. As such, the pressure threshold array may output a specific pressure threshold PT value for each of the regions Ra, Rb, Rc, and Rd.

Also shown in FIG. 3B, the step 62' includes a step 72 of outputting the first indicator 48 based on whether the amount of pressure at each of the at least two regions exceeds the pressure threshold PT. FIG. 6A illustrates an instance where the first indicator 48 includes the numerical indicator 51 based on the amount of pressure between the surface electrode 16 and the target tissue 28 at the first and second regions 16*a*, 16*b*. For example, the first indicator 48 indicates that the amount of pressure at the first region 16*a* exceeds the pressure threshold PT. In an instance where the at least two regions are the regions Ra, Rb, Rc, and Rd of FIG. 4B, the controller 22 may determine that the amount of pressure at the regions Ra and Rb exceeds the pressure threshold PT during step 70. As shown in FIG. 6A, the output device 24 may then output the first indicator 48 including the numerical indicator 51 during step 72 to indicate that the amount of pressure at the first region 16*a* is too high and exceeds the pressure threshold PT. In this way, the numerical indicator 51 of the first indicator 48 indicates that the ET tube 14 should be urged distally to facilitate proper placement.

FIG. 7D illustrates an instance where the first indicator 48 includes the indication of the adjustment 53 based on the amount of pressure between the surface electrode 16 and the target tissue at the third and fourth regions 16*c*, 16*d*. For example, the controller 22 may determine that the amount of pressure at Ra and Rc exceeds the pressure threshold PT during step 70. The output device 24 may then output the first indicator 48 including the indication of the adjustment 53 during step 72 to indicate that the ET tube 14 should be rotated clockwise A1 to facilitate proper placement.

It will be further appreciated that the terms "include," "includes," and "including" have the same meaning as the terms "comprise," "comprises," and "comprising."

Several examples have been discussed in the foregoing description. However, the examples discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

Clauses for Additional Configurations

I. A method of operating an intraoperative nerve monitoring system for monitoring nerve activity within a trachea of a patient, the intraoperative nerve monitoring system includes a console having a controller and an output device and an endotracheal (ET) tube assembly including an ET tube having an outer circumferential surface, a surface electrode wrapped about a portion of the outer circumferential surface of the ET tube, and a pressure sensor assembly coupled to the outer circumferential surface of the ET tube, the method comprising steps of:

inserting the ET tube within the trachea of the patient;
sensing, with the pressure sensor assembly, an amount of pressure between the surface electrode and a target tissue;
determining, with the controller, whether the amount of pressure exceeds a pressure threshold;
outputting, with the output device, a first indicator based on whether the amount of pressure exceeds the pressure threshold to facilitate proper placement of the ET tube in the trachea;
monitoring, with the surface electrode, nerve activity within the trachea while the ET tube is inserted within the trachea; and
outputting, with the output device, a second indicator based on the nerve activity.

II. The method of clause I, wherein the target tissue includes a laryngeal muscle fiber.

III. The method of any preceding clause, wherein the nerve activity includes nerve activity of at least one of a vagus nerve and a laryngeal nerve.

IV. The method of any preceding clause, wherein the step of inserting the ET tube further comprises inserting the ET tube such that the ET tube is rotatable clockwise and counterclockwise within the trachea.

V. The method of any preceding clause, wherein the step of inserting the ET tube further comprises inserting the ET tube such that the ET tube is slidable proximally and distally within the trachea.

VI. The method of any preceding clause, wherein the pressure sensor assembly includes a plurality of pressure sensors such that the step of sensing the amount of pressure comprises sensing the amount of pressure with the plurality of pressure sensors.

VII. The method of any preceding clause, wherein the amount of pressure includes an amount of pressure between the surface electrode and the target tissue at each of at least two regions spaced apart from one another on the outer circumferential surface such that the step of sensing the amount of pressure comprises sensing the amount of pressure at each of the at least two regions.

VIII. The method of any preceding clause, wherein the at least two regions includes four regions spaced apart from one another on the outer circumferential surface.

IX. The method of clause VII, wherein the step of determining whether the amount of pressure exceeds the pressure threshold comprises determining, with the controller, whether the amount of pressure at each of the at least two regions exceeds the pressure threshold.

X. The method of any one of clauses VII-IX, wherein the step of outputting the first indicator comprises outputting the first indicator based on whether the amount of pressure at each of the at least two regions exceeds the pressure threshold.

XI. The method of any preceding clause, wherein the first indicator includes at least one of an audible indicator and a visual indicator.

XII. The method of any preceding clause, wherein the second indicator includes at least one of an audible indicator and a visual indicator.

XIII The method of any preceding clause, wherein the first indicator includes a numerical indicator, and wherein the numerical indicator includes a number based on the amount of pressure between the surface electrode and the target tissue.

XIV. The method of clause VII, wherein the first indicator includes a numerical indicator, and wherein the numerical indicator includes a number based on the amount of pressure between the surface electrode and the target tissue at the at least two regions.

XV. The method of any preceding clause, wherein the first indicator includes an indication of an adjustment to correct a position of the ET tube in the trachea, the adjustment being based on the amount of pressure.

XVI. The method of clause XV, wherein the indication of the adjustment includes at least one of an indication of a clockwise rotation of the ET tube, a counterclockwise rotation of the ET tube, a proximal sliding of the ET tube, and a distal sliding of the ET tube.

XVII. The method of any preceding clause, wherein the step of monitoring nerve activity further comprises sensing, with the surface electrode, electromyography (EMG) signals when the surface electrode contacts the target tissue.

XVIII. The method of any preceding clause, wherein the second indicator includes a waveform corresponding to the nerve activity.

XIX. The method of any preceding clause, wherein the steps of outputting the first indicator and outputting the second indicator comprise concurrently outputting the first indicator and the second indicator.

What is claimed is:

1. An intraoperative nerve monitoring system for monitoring nerve activity within a trachea of a patient, the intraoperative nerve monitoring system comprising:
    an endotracheal (ET) tube assembly, the endotracheal tube assembly comprising:
        an ET tube comprising an outer circumferential surface and a length sufficient for insertion within a trachea of a patient, the ET tube being configured to be at least partially inserted within the trachea;
        a surface electrode wrapped about a portion of the outer circumferential surface of the ET tube, the surface electrode being configured to monitor nerve activity when the ET tube is at least partially inserted within the trachea and is contacting a target tissue and to output a nerve signal corresponding to the nerve activity; and
        a pressure sensor assembly coupled to the outer circumferential surface of the ET tube, the pressure sensor assembly being configured to sense an amount of pressure between the surface electrode and the target tissue at each of at least two regions spaced apart from one another on the outer circumferential surface and output a pressure signal based on the amount of pressure between the surface electrode and the target tissue at each of the at least two regions; and
    a console comprising:
        a controller configured to;
            receive the pressure signal and the nerve signal;
            determine whether the amount of pressure at each of the at least two regions exceeds a pressure threshold based on the pressure signal; and
            output an output signal based on the pressure signal and the nerve signal; and
        an output device configured to receive the output signal and output a first indicator and a second indicator based on the output signal, the first indicator comprising a numerical indicator comprising a number based on the amount of pressure between the surface electrode and the target tissue at the at least two regions to facilitate proper placement of the ET tube in the trachea and the second indicator being indicative of the nerve activity.

2. The intraoperative nerve monitoring system of claim 1, wherein the target tissue comprises a laryngeal muscle fiber.

3. The intraoperative nerve monitoring system of claim 1, wherein the nerve activity comprises a nerve activity of at least one of a vagus nerve and a laryngeal nerve.

4. The intraoperative nerve monitoring system of claim 1, wherein the ET tube is further configured to be at least partially inserted within the trachea such that the ET tube is rotatable clockwise and counterclockwise within the trachea and such that the ET tube is slidable proximally and distally within the trachea.

5. The intraoperative nerve monitoring system of claim 1, wherein the at least two regions comprise four regions spaced apart from one another on the outer circumferential surface.

6. The intraoperative nerve monitoring system of claim 1, wherein the output device is further configured to output the first indicator based on whether the amount of pressure at each of the at least two regions exceeds the pressure threshold.

7. The intraoperative nerve monitoring system of claim 1, wherein the first indicator comprises at least one of an audible indicator and a visual indicator and wherein the second indicator comprises at least one of an audible indicator and a visual indicator.

8. The intraoperative nerve monitoring system of claim 1, wherein the first indicator comprises an indication of an adjustment to correct a position of the ET tube in the trachea, the adjustment being based on the amount of pressure between the surface electrode and the target tissue, and wherein the indication of the adjustment comprises at least one of an indication of a clockwise rotation of the ET tube, a counterclockwise rotation of the ET tube, a proximal sliding of the ET tube, and a distal sliding of the ET tube.

9. The intraoperative nerve monitoring system of claim 1, wherein the surface electrode comprises a plurality of electrode contacts, the electrode contacts being configured to sense electromyography (EMG) signals when the surface electrode contacts the target tissue.

10. The intraoperative nerve monitoring system of claim 1, wherein the second indicator comprises a waveform corresponding to the nerve activity.

11. The intraoperative nerve monitoring system of claim 1, wherein the output device is further configured to output the first indicator and the second indicator concurrently.

12. An intraoperative nerve monitoring system for monitoring nerve activity within a trachea of a patient, the intraoperative nerve monitoring system comprising:
    an endotracheal (ET) tube assembly, the endotracheal tube assembly comprising:
        an ET tube comprising an outer circumferential surface and a length sufficient for insertion within a trachea of a patient, the ET tube being configured to be at least partially inserted within the trachea;
        a surface electrode wrapped about a portion of the outer circumferential surface of the ET tube, the surface electrode being configured to monitor nerve activity when the ET tube is at least partially inserted within the trachea and is contacting a target tissue and to output a nerve signal corresponding to the nerve activity; and
        a pressure sensor assembly coupled to the outer circumferential surface of the ET tube, the pressure sensor assembly being configured to sense an amount of pressure between the surface electrode and the target tissue and output a pressure signal based on the amount of pressure; and
    a console comprising:
        a controller configured to receive the pressure signal and the nerve signal and output an output signal based on the pressure signal and the nerve signal; and
        an output device configured to receive the output signal and output a first indicator and a second indicator concurrently based on the output signal, the first indicator being configured to facilitate proper placement of the ET tube in the trachea and the second indicator being indicative of the nerve activity.

13. The intraoperative nerve monitoring system of claim 12, wherein the target tissue comprises a laryngeal muscle fiber.

14. The intraoperative nerve monitoring system of claim 12, wherein the nerve activity comprises a nerve activity of at least one of a vagus nerve and a laryngeal nerve.

15. The intraoperative nerve monitoring system of claim 12, wherein the ET tube is further configured to be at least partially inserted within the trachea such that the ET tube is rotatable clockwise and counterclockwise within the trachea and such that the ET tube is slidable proximally and distally within the trachea.

16. The intraoperative nerve monitoring system of claim 12, wherein the amount of pressure comprises an amount of pressure between the surface electrode and the target tissue at each of at least two regions spaced apart from one another on the outer circumferential surface such that the pressure sensor assembly is configured to sense the amount of pressure at each of the at least two regions, wherein the controller is further configured to determine whether the amount of pressure at each of the at least two regions exceeds a pressure threshold.

17. The intraoperative nerve monitoring system of claim 12, wherein the first indicator comprises at least one of an audible indicator and a visual indicator and wherein the second indicator comprises at least one of an audible indicator and a visual indicator.

18. The intraoperative nerve monitoring system of claim 12, wherein the first indicator comprises an indication of an adjustment to correct a position of the ET tube in the trachea, the adjustment being based on the amount of pressure between the surface electrode and the target tissue, and wherein the indication of the adjustment comprises at least one of an indication of a clockwise rotation of the ET tube, a counterclockwise rotation of the ET tube, a proximal sliding of the ET tube, and a distal sliding of the ET tube.

19. The intraoperative nerve monitoring system of claim 12, wherein the surface electrode comprises a plurality of electrode contacts, the electrode contacts being configured to sense electromyography (EMG) signals when the surface electrode contacts the target tissue.

20. The intraoperative nerve monitoring system of claim 12, wherein the second indicator comprises a waveform corresponding to the nerve activity.

* * * * *